(12) United States Patent
Vardy et al.

(10) Patent No.: US 11,219,588 B2
(45) Date of Patent: Jan. 11, 2022

(54) USE OF POLYAMINES IN COMPOSITIONS AND METHODS FOR INDUCING OR PROMOTING SKIN DARKENING AND REGULATING MELANOGENESIS

(71) Applicant: Agency for Science, Technology and Research, Singapore (SG)

(72) Inventors: Leah Vardy, Singapore (SG); Aishwarya Sridharan, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 16/331,952

(22) PCT Filed: Sep. 8, 2017

(86) PCT No.: PCT/SG2017/050452
§ 371 (c)(1),
(2) Date: Mar. 8, 2019

(87) PCT Pub. No.: WO2018/048358
PCT Pub. Date: Mar. 15, 2018

(65) Prior Publication Data
US 2019/0216702 A1 Jul. 18, 2019

(30) Foreign Application Priority Data
Sep. 8, 2016 (SG) .......................... 10201607498Y

(51) Int. Cl.
| | |
|---|---|
| *A61K 8/41* | (2006.01) |
| *A61Q 19/02* | (2006.01) |
| *A61Q 19/04* | (2006.01) |
| *A61K 31/132* | (2006.01) |
| *A61P 17/00* | (2006.01) |
| *A61K 9/00* | (2006.01) |
| *A61K 8/44* | (2006.01) |

(52) U.S. Cl.
CPC .................. *A61K 8/41* (2013.01); *A61K 8/44* (2013.01); *A61K 9/0014* (2013.01); *A61K 31/132* (2013.01); *A61P 17/00* (2018.01); *A61Q 19/02* (2013.01); *A61Q 19/04* (2013.01)

(58) Field of Classification Search
None
See application file for complete search history.

(56) References Cited

U.S. PATENT DOCUMENTS

| 2008/0124312 A1* | 5/2008 | Lovaas ................... A61K 8/41 424/94.1 |
|---|---|---|
| 2010/0278784 A1 | 11/2010 | Pojasek et al. | |
| 2011/0033403 A1 | 2/2011 | Lee et al. | |

OTHER PUBLICATIONS

Ebanks et al (Int J Mol Sci, 2009, 10, 4066-4087). (Year: 2009).*
Frohnhofer, et al., "Spermidine, but not spermine, is essential for pigment pattern formation in zebrafish," Biology Open, 2016, pp. 736-744, vol. 5, The Company of Biologists Ltd.
Grossi, et al., "Inhibition of Polyamine Uptake Potentiates the Anti-Proliferative Effect of Polyamine Synthesis Inhibition and Preserves the Contractile Phenotype of Vascular Smooth Muscle Cells," Journal of Cellular Physiology, 2016, pp. 1334-1342, vol. 231, Wiley Periodicals, Inc.
Kapyaho, et al., "Stimulation of Melanotic Expression in Murine Melanoma Cells Exposed to Polyamine Antimetabolites," Biochemical and Biophysical Research Communications, May 31, 1983, pp. 18-23, vol. 113, Helsinki, Finland.
Kapyaho, et al., "Effects of Inhibitors of Polyamine Biosynthesis on the Growth and Melanogenesis of Murine Melanoma Cells," Cancer Research, Apr. 1985, pp. 1444-1448, vol. 45, The American Association for Cancer Research.
Mcewan, et al., "Inhibition of Melanization in Human Melanoma Cells by a Serotonin Uptake Inhibitor," The Journal of Investigative Dermatology, Jul. 1987, pp. 82-86, vol. 89, No. 1, The Society for Investigative Dermatology, Inc.
Sunkara, et al., "Effect of Inhibition of Polyamine Biosynthesis by DL-$\alpha$-Difluoromethylornithine on the Growth and Melanogenesis of B16 Melanoma in Virto and in Vivo," Cancer Research, Sep. 1985, pp. 4067-4070, vol. 45, American Association for Cancer Research.
Xie, et al., "NNAMB, a novel homospermidine conjugate, induces apoptosis and differentiation in B16 Melanoma cells," Chinese Pharmacological Bulletin, Oct. 23, 2007, pp. 1285-1290, vol. 10.
International Search Report & Written Opinion of the International Searching Authority dated Nov. 28, 2017, for PCT application No. SG2017/050452.
SRIDHARAN et al., "Role of Polyamines In Melanogenesis of the Human Skin", TDA-ASPCR, Nov. 10, 2016, 1 page.
Zhou et al., "Inhibitory Effect of a Genistein Derivative on Pigmentation of Guinea Pig Skin", RSC Advances, Jan. 13, 2017, 4 pages, vol. 7, No. 13.
Linsalata et al., "Effects of Genistein on the Polyamine Metabolism and Cell Growth in DLD-1 Human Colon Cancer Cells", May 1, 2005, 12 pages, vol. 52, No. 1.
Khomutov et al., "Hydroxylamine Derivatives for Regulation c-f Spermine and Spermidine Metabolism". Jul. 17, 2013, 16 pages, vol. 78, No. 13.
Yang et al., "The Effect of Genistein on Melanin Synthesis and In Vivo Whitening", Microbiology and Biotechnology Letters: Korea Science, Jan. 1, 2008, 10 pages, Voi. 36, No. 1.

(Continued)

*Primary Examiner* — Celeste A Roney
(74) *Attorney, Agent, or Firm* — Womble Bond Dickinson (US) LLP

(57) ABSTRACT

The present disclosure provides a method of inducing or promoting darkening of the skin and/or melanogenesis, a method of treating a skin condition or disorder, in particular hypopigmentation, comprising administration of a polycationic aliphatic amine, wherein said polycationic aliphatic amine preferably is putrescine, spermidine and spermine. The invention further includes corresponding methods of reducing or preventing darkening of skin and/or melanogenesis, or related methods of treating a skin condition or disorder, comprising administration of at least an inhibitor of polycationic aliphatic amine transport or synthesis, wherein said inhibitor is preferably trimer44NMe or difluoromethylornithine (DFMO) respectively.

18 Claims, 12 Drawing Sheets
Specification includes a Sequence Listing.

(56) References Cited

OTHER PUBLICATIONS

Muth et al., "Polyamine Transport inhibitors: Design, Synthesis, and Combination Therapies with Difluoromethylornithine", Journal of Medicinal Chemistry, Jan. 9, 2014, vol. 57, No. 2.
The International Preliminary Report on Patentability for PCT Counterpart Application No. PCT/SG2017/050452, dated Mar. 12, 2019, 7 pages.
The Extended European Search Report for European Patent Application No. 17849215.3, dated Jun. 12, 2020, 18 pages.

* cited by examiner

A

Untreated    Putrescine treated

B

Untreated

Putrescine treated

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: TYR forward primer

<400> SEQUENCE: 1
tgcacagaga gacgactctt g                                              21

<210> SEQ ID NO 2
<211> LENGTH: 21
<212> TYPE: DNA
<213> ORGANISM: Artificial Sequence
<220> FEATURE:
<223> OTHER INFORMATION: TYR reverse primer

<400> SEQUENCE: 2
ggcatggact gtggtcatga g                                              21

<210> SEQ ID NO 3
<211> LENGTH: 22
<212> TYPE: DNA
<213> ORGANISM: Artificial Sequence
<220> FEATURE:
<223> OTHER INFORMATION: TYRP1 forward primer

<400> SEQUENCE: 3
tctctgggct gtatcttctt cc                                             22

<210> SEQ ID NO 4
<211> LENGTH: 21
<212> TYPE: DNA
<213> ORGANISM: Artificial Sequence
<220> FEATURE:
<223> OTHER INFORMATION: TYRP1 reverse primer

<400> SEQUENCE: 4
gtctgggcaa cacataccac t                                              21

<210> SEQ ID NO 5
<211> LENGTH: 20
<212> TYPE: DNA
<213> ORGANISM: Artificial Sequence
<220> FEATURE:
<223> OTHER INFORMATION: DCT forward primer

<400> SEQUENCE: 5
cttgggctgc aaaatcctgc                                                20

<210> SEQ ID NO 6
<211> LENGTH: 21
<212> TYPE: DNA
<213> ORGANISM: Artificial Sequence
<220> FEATURE:
<223> OTHER INFORMATION: DCT reverse primer

<400> SEQUENCE: 6
cagcactcct tgttcactag g                                              21

<210> SEQ ID NO 7
<211> LENGTH: 23
<212> TYPE: DNA
<213> ORGANISM: Artificial Sequence
```

```
<220> FEATURE:
<223> OTHER INFORMATION: PMEL forward primer

<400> SEQUENCE: 7
agtgcctact acagaagttg tgg                                               23

<210> SEQ ID NO 8
<211> LENGTH: 21
<212> TYPE: DNA
<213> ORGANISM: Artificial Sequence
<220> FEATURE:
<223> OTHER INFORMATION: PMEL reverse primer

<400> SEQUENCE: 8
cacaggtgca gtgcttatga c                                                 21
```

USE OF POLYAMINES IN COMPOSITIONS AND METHODS FOR INDUCING OR PROMOTING SKIN DARKENING AND REGULATING MELANOGENESIS

This patent application is a U.S. National Phase Application Under 35 U.S.C. § 371 of International Application No. PCT/SG2017/050452, filed 8 Sep. 2017, entitled USE OF POLYAMINES IN COMPOSITIONS AND METHODS FOR INDUCING OR PROMOTING SKIN DARKENING AND REGULATING MELANOGENESIS, which claims the benefit of priority of Singapore application No. 10201607498Y, filed on 8 Sep. 2016, the contents of which were incorporated by reference in the entirety for all purposes.

INCORPORATION BY REFERENCE

This patent application incorporates by reference the material (i.e., Sequence Listing) in the ASCII text file named 9322P159_Sequence_Listing.txt, created on Mar. 7, 2019, having a file size of 4,096 bytes.

FIELD OF THE INVENTION

The present invention generally relates to the field of biochemistry. It is referred herein to pharmaceutical compositions and methods, in particular pharmaceutical compositions and methods that induce or promote darkening of the skin and regulate melanogenesis.

BACKGROUND OF THE INVENTION

Melanin is a naturally occurring pigment, which determines the skin, hair and eye colour of human beings. The process of melanin production is called melanogenesis. It occurs in highly specialized cells called melanocytes, which are present in the basal layer of the epidermis. There are about 1000-2000 melanocytes per square mm of the skin, which constitute about 5-10% of the total cells present in the skin. Melanin production and distribution is the result of a symbiotic relationship between melanocytes and the surrounding keratinocytes, which together make up the Epidermal Melanin Unit (EMU). Each EMU is comprised of 1 melanocyte surrounded by approximately 40 keratinocytes in the basal and suprabasal layers of the epidermis. The EMU responds to a wide range of external and internal stimuli through paracrine or autocrine systems.

Melanogenesis can be stimulated by, for example, ultraviolet (UV) light. UV-induced melanogenesis is skin's major defense against further UV damage. More specifically, melanin pigmentation protects against UV damage by absorbing UV photons and UV-generated free radicals before they can react with DNA and other critical cellular components. However, cumulative exposure to UV light can result in an increased risk of skin cancer and skin damage (e.g., premature aging and wrinkles). Thus, pharmaceutical agents that induce melanogenesis are of medical interest for protecting skin from photodamage without UV exposure or the risk of skin cancer. The benefit can be extended to addressing certain cosmetic needs for tanning, especially sunless tanning.

Pharmaceutical agents that regulate melanogenesis can also address certain skin pigmentation disorders. Skin pigmentation disorders include, for example, hyper-pigmentation and hypo-pigmentation. Hyper-pigmentation (excessive pigmentation) can be associated with inflammatory responses, yeast infections, pregnancy and aging, etc. The counterpart to this condition is known as hypo-pigmentation, where there is a reduction or absence of pigmentation. In its most extreme form, hypo-pigmentation is represented by albinism, an inherited condition where there is a complete absence of skin pigment due to absence or defect in an enzyme involved in the production of melanin. Another form of hypo-pigmentation is vitiligo, characterized by light patches on the skin. Thus, pharmaceutical agents that regulate melanogenesis could be effective therapy for skin pigmentation disorders.

Thus, there is a continuing need for an effective therapy for treating or preventing photodamage and skin pigmentation disorders, as well as addressing cosmetic needs for sunless tanning.

SUMMARY OF THE INVENTION

In one aspect, there is provided a method of inducing or promoting darkening of the skin and/or melanogenesis, the method comprising administering at least one polycationic aliphatic amine in a pharmaceutically effective amount to a subject in need thereof.

In another aspect, there is provided a method of treating a skin condition or disorder, the method comprising administering at least one polycationic aliphatic amine in a pharmaceutically effective amount to a subject in need thereof, wherein the skin condition or disorder comprises hypopigmentation. In some examples, the skin condition or disorder is selected from the group consisting of vitiligo, depigmentation, hypopigmentation, focal hypopigmentation, post-inflammatory hypopigmentation, piebaldism, albinism, pityriasis alba, tinea versicolor, photosensitivity, leucism, idiopathic guttate hypomelanosis, progressive macular hypomelanosis, atopic dermatitis, psoriasis, and guttate parapsoriasis.

In some examples, the polycationic aliphatic amine comprises at least 2, or at least 3, or at least 4, or at least 5 amino groups. In some examples, if the polycationic aliphatic amine has at least 2 or more amino groups, two amino groups are terminal amino groups. In some examples, if the polycationic aliphatic amine has at least 3 or more amino groups, at least one of the amino groups of the polycationic aliphatic amine is a secondary amino group. In some examples, the polycationic aliphatic amine is selected from the group consisting of putrescine, spermidine, spermine and combinations thereof.

In some examples, the pharmaceutically effective amount of polycationic aliphatic amine is between about 3 mmol to 12 mmol.

In a further aspect, there is provided a method of reducing or preventing darkening of the skin and/or melanogenesis, the method comprising administering at least one inhibitor of polycationic aliphatic amine in a pharmaceutically effective amount to a subject in need thereof.

In some examples, the subject is suffering from darkening of the skin and/or melanogenesis associated with pregnancy, inflammation, yeast infection, or aging.

In some examples, the at least one inhibitor of polycationic aliphatic amine is selected from the group consisting of: an inhibitor of the transport of polycationic aliphatic amine, an inhibitor of the synthesis of polycationic aliphatic amine, an inhibitor of the catabolism of polycationic aliphatic amine, and combinations thereof. In one example, the inhibitor of the transport of polycationic aliphatic amine is trimer44NMe. In another example, the inhibitor of the synthesis of polycationic aliphatic amine is difluoromethylornithine (DFMO).

In some examples, the at least one polycationic aliphatic amine or the at least one inhibitor of polycationic aliphatic amine is administered in a pharmaceutical composition, wherein the pharmaceutical composition is administered intradermally, cutaneously, subcutaneously, topically, transdermally, or any combination thereof. In some examples, the pharmaceutical composition is provided as pastes, powders, dressings, creams, plasters, solutions, patches, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof. In one example, the pharmaceutical composition is a dermatological composition.

In one example, the method provided herein is used for cosmetic purposes.

BRIEF DESCRIPTION OF THE DRAWINGS

The invention will be better understood with reference to the detailed description when considered in conjunction with the non-limiting examples and the accompanying drawings, in which:

FIG. 1A top panel is a representative image of NHEM-aLP cells (normal human foreskin-derived epidermal melanocyte cells) in 6 well plate, untreated (left) versus treated with 2 mM putrescine (right). Visually, it can be seen that the treated cells appear darker when compared with the untreated cells. FIG. 1B is a representative tissue culture image of untreated cells (top) versus 2 mM putrescine treated cells (bottom) at day 6 post treatment at 4× and 10× magnification, respectively. Cells became larger and flatter, and displayed an increased number of dendrites (arrows). This phenotype (that is, the formation of dendrites due to putrescine treatment) is typically observed on treatment of NHEM with the melanogenic agents α-MSH, ACTH or endothelin-1, where the bipolar or tripolar melanocytes become more dendritic upon treatment. FIG. 1C is a representative image of cell lysate before melanin quantification (top) and average values of the percentage melanin content in cells treated with 2 mM putrescine for 6 days after normalizing to the control (bottom) (n=15; from 4 independent experiments). *$p<0.001$. Error bar is mean±SEM. The results shown in FIG. 1** show that treatment with the polycationic aliphatic amine putrescine increases the melanin content of normal human primary epidermal melanocytes from adult light pigmented donor (NHEM-aLP) cells.

FIG. 2A is a bar graph showing relative mRNA expression levels determined by real time PCR of melanogenesis-related genes (TYR, TYRP1, DCT and PMEL) with respect to the house keeping genes RPLP0 in the NHEM-aLP cells, without and with 2 mM putrescine treatment for 6 days. Significant increase in the relative mRNA levels is seen in all melanogenesis-related genes after treatment. (n=9; from 3 independent experiments). $p<0.01$, *$p<0.001$. Error bar is mean±SEM. FIG. 2B shows representative western blot images showing the expression levels of melanogenesis related proteins (TYR, TYRP1 and DCT) from cell lysates of putrescine untreated and treated NHEM-aLP cells (n=3). A significant increase in the melanogenesis-related protein expression levels were seen in all putrescine treated samples. The results shown in FIG. 2 show that putrescine treatment increases expression of melanogenesis-related genes and proteins in NHEM-aLP cells.

DETAILED DESCRIPTION OF THE PRESENT INVENTION

Figure 1:
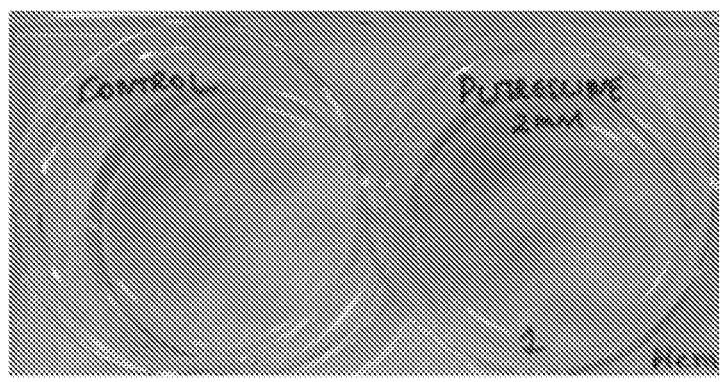
FIG. 1 shows the effect of putrescine treatment on the melanin content in cell culture.
Figure 1:
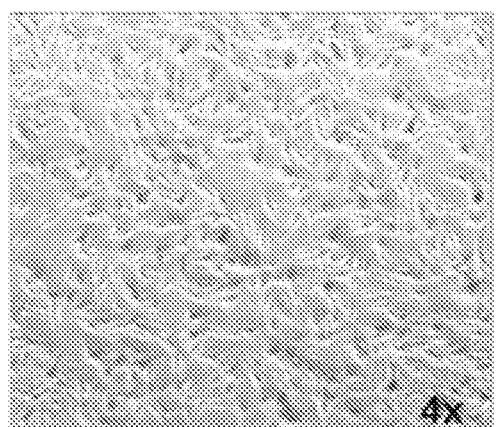
Figure 1:
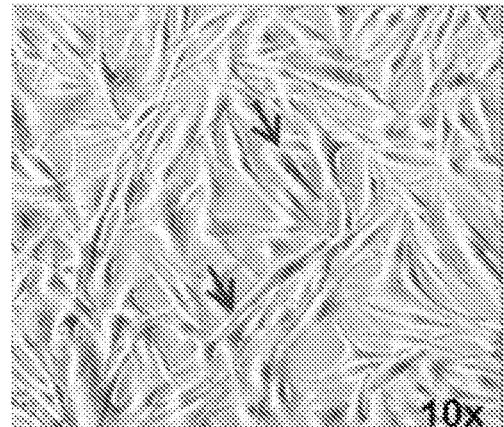
Figure 1:
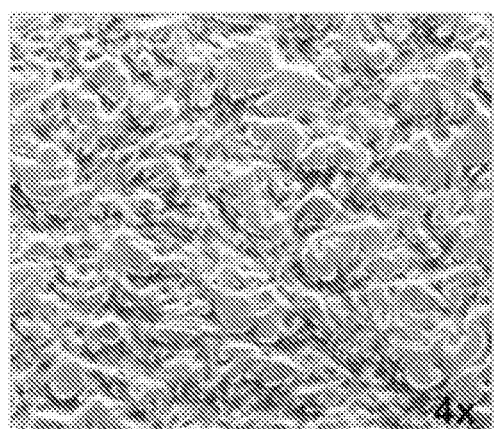
Figure 1:
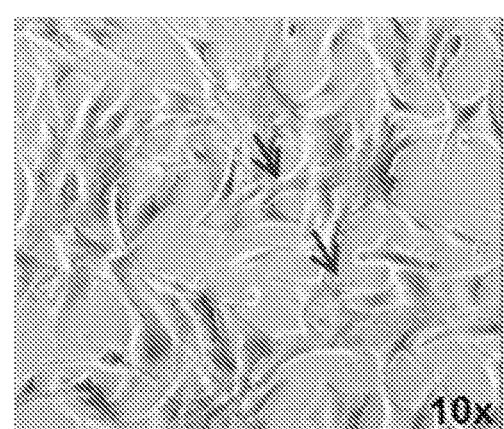
Figure 1:
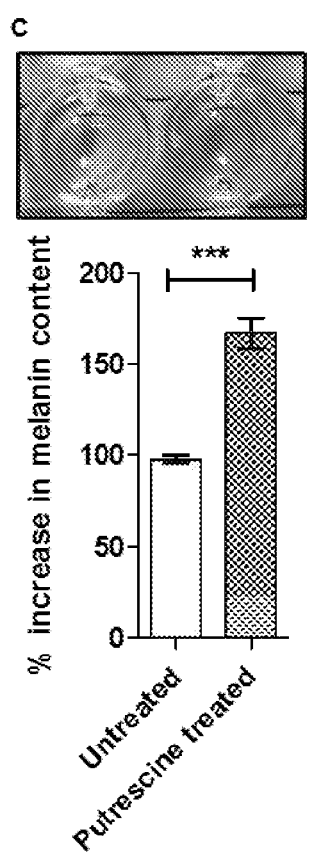

The inventors of the present disclosure have set out to provide alternative pharmaceutical compositions and methods for regulating melanogenesis and for inducing or promoting darkening of the skin.

In a first aspect, there is provided a method of inducing or promoting darkening of the skin and/or melanogenesis, the method comprising administering at least one polycationic aliphatic amine in a pharmaceutically effective amount to a subject in need thereof.

The term "melanogenesis" as used herein refers to the process of producing melanin by melanocytes. Melanogenesis leads to a long-lasting pigmentation, which is in contrast to the pigmentation that originates from oxidation of existing melanin. Exposure to UV-B radiation causes increased melanogenesis. Melanogenesis can protect the hypodermis, the layer under the skin, from the DNA photodamage caused by UV-B light. In one specific example, melanogenesis takes place in the melanocytes located in the skin.

It is known that melanogenesis also occurs in places other than the skin, for example, in hair follicles. However, as also known in the art, there are differences between epidermal pigmentation, follicular pigmentation, and their respective melanocytes, all of which is well documented and reviewed in the art. Without being bound by theory, the differences between epidermal and follicular pigmentation can be summarized as follows:

Melanogenesis in follicular pigmentation is understood to be stringently coupled to the hair growth cycle, while melanogenesis in the epidermal pigmentation is understood to be continuous, and augmentable;

Despite their common and shared origin in the early epidermis, the melanogenically active melanocytes in the anagen hair bulb are larger, and with longer dendrites, than melanogenically active pigment cells in the epidermis. Melanogenically active melanocytes in the anagen hair bulb also have more extensive Golgi apparatus and rough endoplasmic reticulum, and produce larger melanosomes than epidermal melanocytes;

While eumelanin produced by the epidermal melanocytes degrades almost completely in the differentiating layers of the epidermis, eumelanin granules transferred into hair cortical keratinocytes remain minimally digested. Hence, in the latter, the proximal and distal ends of a typical scalp hair shaft are similarly pigmented. This difference may relate to the significantly larger melanosome size in follicular melanocytes (approximately $0.35 \times 1.0$ μm$^2$ for Caucasian eumelanosomes) than epidermal melanocytes (approximately $0.25 \times 0.6$ μm$^2$ for Caucasian eumelanosomes). This parameter will influence the nature of their uptake by recipient keratinocytes and their relative susceptibilities to enzymatic degradation. This may be analogous to the enhanced survival of larger melanosomes in black skin compared with their white counterparts.

Additionally, it is also known in that art that follicular melanin units lacks a major melanogenesis related protein, TRP2, which is said to be present in abundance in all epidermal melanin units, irrespective of the skin type.

Taken altogether, this information shows that is considered to be well-established and documented in the art that there are conceptual differences between the melanogenesis and melanocytes in the epidermal and follicular melanin units.

The term "melanocyte" as used herein refers to melanin-producing cells located in the bottom layer (the stratum basale) of the skin's epidermis, the middle layer of the eye (the uvea), the inner ear, meninges, bones and heart. Each epidermal melanocyte is associated with a group of neighboring keratinocytes, forming an epidermal melanocyte unit.

The term "melanin" as used herein is a broad term for a group of natural pigments found in most organisms. Melanin is produced by the oxidation of the amino acid tyrosine, followed by polymerization. Melanin is produced in melanocytes and subsequently transported to the keratinocytes through dendrites.

The term "keratinocyte" as used herein refers to the predominant cell type in the epidermis, which constitutes 90% of the cells found in the epidermis. The primary function of keratinocyte is the formation of a barrier against environmental damage. Keratinocytes contribute to protecting body from UV radiation by taking up melanosomes, which are vesicles containing melanin. The melanin is then stored within keratinocytes.

The term "amine" as used herein refers to a compound or functional group that contains a basic nitrogen atom with a lone electron pair.

The term "aliphatic amine" as used herein refers to an amine in a molecule of which there are no aromatic rings directly on the nitrogen atom of the amine.

As used herein, the term "polycationic aliphatic amine" refers to an open chained organic compound, comprising an amine group and one or more positive charges.

In some examples, the polycationic aliphatic amine comprises at least 2, or at least 3, or at least 4, or at least 5 amino groups. In some examples, wherein if the polycationic aliphatic amine has at least 2 or more amino groups, two of the amino groups are terminal amino groups. In some examples, if the polycationic aliphatic amine has at least 3 or more amino groups, at least one of the amino groups of the polycationic aliphatic amine is a secondary amino group.

In some specific examples, the polycationic aliphatic amine is selected from the group consisting of putrescine, spermidine, spermine, and combinations thereof. The combinations could be, for example, the combination of putrescine and spermidine, the combination of putrescine and spermine, the combination of spermidine and spermine, and the combination of putrescien, spermidine and spermine.

The term "putrescine" as used herein is also known as tetramethylenediamine, butane-1,4-diamine, or 1,4-diaminobutane. It is an amine represented by the formula $NH_2(CH_2)_4NH_2$ or

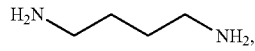

and has a molecular weight of about 161.07 g/mol.

The term "spermidine" as used herein is also known as N'-(3-aminopropyl)butane-1,4-diamine. It is an amine represented by the formula $NH_2(CH_2)_3NH(CH_2)_4NH_2$ or

The term "spermine" as used herein is also known as N,N'-bis(3-aminopropyl)butane-1,4-diamine. It is an amine represented by the formula $NH_2(CH_2)_3NH(CH_2)_4$ $NH(CH_2)_3NH_2$ or

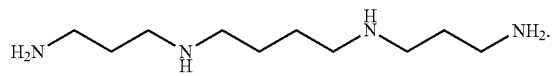 [SMILES: NCCCNCCCCNCCCN]

Spermidine synthase (SPDS) catalyzes the formation of spermidine from putrescine. Spermidine is a precursor to spermine. Biosynthesis of spermidine and spermine from putrescine is shown in the following scheme (Ado=5'-adenosyl).

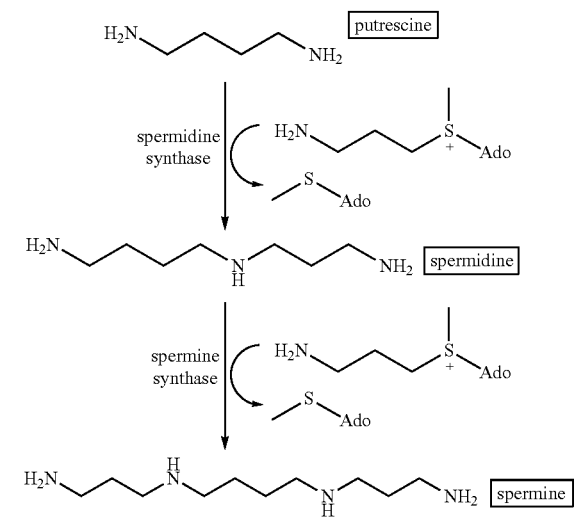

The term "pharmaceutically effective amount" as used herein refers the amount of an active ingredient that, when administered to a subject in need thereof, is sufficient to exert the claimed effect. The "pharmaceutically effective amount" will vary depending on the active ingredient being administered, the age, weight, physical condition and responsiveness of the subject in need thereof.

In some examples of the first aspect, the pharmaceutically effective amount of polycationic aliphatic amine being administered is between 0.3 mmol to 12 mmol, or between 0.3 mmol to 3 mmol, or between 3 mmol to 12 mmol, or between 3 mmol to 6 mmol, or between 6 mmol to 12 mmol, or between 4.5 mmol to 5.4 mmol, or between 3.6 mmol to 4.8 mmol, or between 5.4 mmol to 10.5 mmol, or between 9 mmol to 11.4 mmol, or at about 3.3 mmol, or about 3.6 mmol, or about 3.9 mmol, or about 4.8 mmol, or about 5.4 mmol, or about 7.5 mmol, or about 10.8 mmol. In some examples, the concentration of polycationic aliphatic amine is between 0.05 mM to 2 mM, or between 0.05 mM to 0.5 mM, or between 0.5 mM to 2 mM, or between 0.5 mM to 1 mM, or between 1 mM to 2 mM, or between 0.75 mM to 0.9 mM, or between 0.6 mM to 0.8 mM, or between 0.9 mM to 1.75 mM, or between 1.5 mM to 1.9 mM, or at about 0.55 mM, or about 0.6 mM, or about 0.65 mM, or about 0.8 mM, or about 0.9 mM, or about 1.25 mM, or about 1.8 mM. In one specific example, the pharmaceutically effective amount of polycationic aliphatic amine being administered is 3 mmol, and the concentration is 0.5 mM. In another specific example, the pharmaceutically effective amount of polycationic aliphatic amine being administered is 12 mmol, and the concentration is 2 mM. In the experiments as provided in the present application, the concentration of, for example, putrescine, was between 0.5 mM to 2 mM. Thus, in some examples, the concentration of putrescine is less than 2 mM. In other examples, the concentration of putrescine is about 2 mM.

In some specific examples, the polycationic aliphatic amine being administered is putrescine, whereby the pharmaceutically effective amount being administered is between 3 mmol to 12 mmol, and the concentration is between 0.5 mM to 2 mM. In one specific example, the pharmaceutically effective amount of putrescine being administered is 3 mmol and the concentration is 0.05 mM. In another specific example, the pharmaceutically effective amount of putrescine being administered is 12 mmol and the concentration is 2 mM.

In some specific examples, the polycationic aliphatic amine being administered is spermidine, whereby the pharmaceutically effective amount being administered is between 3 mmol to 12 mmol, and the concentration is between 0.5 mM to 2 mM. In one specific example, the pharmaceutically effective amount of spermidine being administered is 3 mmol and the concentration is 0.05 mM. In another specific example, the pharmaceutically effective amount of spermidine being administered is 12 mmol and the concentration is 2 mM.

In some specific examples, the polycationic aliphatic amine being administered is spermine, whereby the pharmaceutically effective amount being administered is between 3 mmol to 12 mmol, and the concentration is between 0.5 mM to 2 mM. In one specific example, the pharmaceutically effective amount of spermine being administered is 3 mmol and the concentration is 0.05 mM. In another specific example, the pharmaceutically effective amount of spermine being administered is 12 mmol and the concentration is 2 mM. In one example, more than one polycationic aliphatic amine is used, such as a mixture of different polycationic aliphatic amines, e.g. a mixture of spermidine with spermine and putrescine; spermidine with putrescine; spermidine with spermine; or putrescine with spermine. The concentration of each polycationic aliphatic amine is as described herein for a single polycationic aliphatic amine or the amounts and concentrations described herein are the sum of the amounts and concentrations of each of the polycationic aliphatic amines in a mixture.

The at least one polycationic aliphatic amine can be administered in a pharmaceutical composition. In some examples, the pharmaceutical composition could be administered intradermally, cutaneously, subcutaneously, topically, transdermally, or any combination thereof.

In some examples, the pharmaceutical composition further comprises a pharmaceutically acceptable carrier and/or a pharmaceutically acceptable salt.

The pharmaceutical composition can be provided in various forms, the non-limiting examples of which include pastes, powders, dressings, creams, plasters, solutions, patches, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof. In one specific example, the pharmaceutical composition is provided as a dermatological composition. Also, depending on the location to be treated and the intended route of administration, the pharmaceutical composition disclosed herein can further comprise a pharmaceutically acceptable carrier and/or a pharmaceutically acceptable salt.

In one example, the composition for topical administration comprises the composition as described herein and a dermatologically acceptable vehicle. The vehicle may be aqueous or non-aqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous non-aqueous or oil phase (oil-in-water emulsion), or a continuous non-aqueous or oil phase and a discontinuous aqueous phase (water-in-oil emulsion).

The pharmaceutical excipients used in the topical preparation of the present disclosure may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for a hydrophobic topical formulation include mineral oils, vegetable oils, and silicone oils. If desired, the composition as described herein may be dissolved or dispersed in a hydrophobic oil phase, and the oil phase may then be emulsified in an aqueous phase comprising water, alone or in combination with lower alcohols, glycerin, and/or glycols.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof, including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polydydric alcohol esters may be used as emulsifiers or emollients. Suitable polydydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing the composition as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the composition as described herein to keratinocytes by fusing with the cell membrane of the keratinocytes.

In one example, the topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

Suitable viscosity enhancers or thickeners which may be used to prepare a viscous gel or cream with an aqueous base include sodium polyacrylate, xanthan gum, polyvinyl pyrollidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols.

Suitable preservatives and/or antioxidants for use in topical formulations include benzalkonium chloride, benzyl alcohol, phenol, urea, parabens, butylated hydroxytoluene (BHT), butylated hydroxyanisole (BHA), Tocopherol, and mixtures thereof.

Suitable chelating agents for use in topical formulations include ethylene diamine tetraacetic acid, alkali metal salts thereof, alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid.

The various examples of creams, ointments, lotions, solutions, gels, sprays and patches may incorporate the composition as described herein as the active ingredient, in combination with penetration enhancing agents and other active agents acting synergistically on the skin for the promotion of inducing or promoting darkening of the skin and/or melanogenesis, a method of treating a skin condition or disorder, and a method of reducing or preventing darkening of the skin and/or melanogenesis.

Promoting darkening of the skin and/melanogenesis can be used for cosmetic purposes, such as sun-less tanning. Thus, in one example, the method of the first aspect can be used for cosmetic purposes only.

In a second aspect, there is provided a method of treating skin conditions or disorders, the method comprising administering at least one polycationic aliphatic amine in a pharmaceutically effective amount to a subject in need thereof. The at least one polycationic aliphatic amine and the pharmaceutically effective amount are as defined above.

The skin conditions to be treated generally involve dysregulation of skin pigmentation, in particular hypopigmentation. The term "hypopigmentation" as used herein refers to the loss of skin color caused by depletion of melanocyte or melanin, or a decrease in the amino acid tyrosine, which is used by melanocytes to make melanin.

In some examples, the skin conditions to be treated include but are not limited to, vitiligo, depigmentation, hypopigmentation, focal hypopigmentation, post-inflammatory hypopigmentation (post-inflammatory hypomelanosis), piebaldism, albinism, pityriasis alba, tinea versicolor, photosensitivity, leucism, idiopathic guttate hypomelanosis, progressive macular hypomelanosis, atopic dermatitis, psoriasis, and guttate parapsoriasis.

The term "vitiligo" as used herein refers to a long-term skin condition characterized by patches of the skin losing their pigment. The patches of skin affected become white and usually have sharp margins.

The term "depigmentation" as used herein generally refers to the lightening of the skin, or loss of pigment. Depigmentation of the skin can be caused by a number of local and systemic conditions. The pigment loss can be partial (e.g. caused by injury to the skin) or complete (e.g. vitiligo). It can be temporary (e.g. tinea versicolor) or permanent (e.g. albinism).

The term "piebaldism" as used herein refers to a rare autosomal dominant disorder of melanocyte development. Common characteristics include a congenital white forelock, scattered normal pigmented and hypopigmented macules and a triangular shaped depigmented patch on the forehead.

The term "albinism" as used herein refers to is a congenital disorder characterized by the complete or partial absence of pigment in the skin, hair and eyes. Albinism is associated with a number of vision defects, such as photophobia, nystagmus, and amblyopia. Lack of skin pigmentation makes the subject more susceptible to sunburn and skin cancers.

The term "pityriasis alba" as used herein refers to a skin disorder that mostly affects children and young adults. The condition may be associated with eczema, a common skin disorder that causes scaly, itchy rashes. People with pityriasis alba develop red or pink patches on their skin that are usually round or oval. The patches usually clear up with moisturizing creams or go away on their own. However, they often leave pale marks on the skin after the redness has faded.

The term "tinea versicolor" as used herein refers to a condition characterized by a skin eruption on the trunk and proximal extremities. The majority of tinea versicolor is caused by the fungus *Malassezia globosa*, although *Malassezia furfur* is responsible for a small number of cases.

The term "photosensitivity" as used herein refers to an immune system reaction that is triggered by sunlight. Photosensitivity reactions include solar urticaria, chemical photosensitization, and polymorphous light eruption and are usually characterized by an itchy eruption on patches of sun-exposed skin.

The term "leucism" as used herein refers to a condition in which there is partial loss of pigmentation, resulting in white, pale, or patchy coloration of the skin or hair, but not the eyes.

The term "idiopathic guttate hypomelanosis" as used herein refers to a benign and asymptomatic skin manifestation characterized as diffuse hypopigmented macules, or white spots. It is most commonly seen in fair-skinned individuals and appears to be related to cumulative sun exposure. The distribution of IGH can be seen along most exposed areas of the body, including areas of the arms, legs, upper back, and face. Lesions are usually seen first along the anterior portion of the legs and then seen on the arms, back and face.

The term "progressive macular hypomelanosis" as used herein refers to a common skin disorder characterized by ill-defined nummular, non-scaly hypopigmented spots on the trunk, often confluent in and around the midline, and rarely extending to the proximal extremities and neck/head region. There is no itch, pain, or preceding inflammation.

The term "atopic dermatitis" as used herein is also known as atopic eczema. It is a type of inflammation of the skin (dermatitis) that results in itchy, red, swollen, and cracked skin. Clear fluid may come from the affected areas, which often thicken over time. The condition typically starts in childhood with changing severity over the years. Scratching worsens symptoms and affected people have an increased risk of skin infections.

The term "psoriasis" as used herein refers to a long-lasting autoimmune disease which is characterized by patches of abnormal skin. These skin patches are typically red, itchy, and scaly. They may vary in severity from small and localized to complete body coverage.

The term "guttate parapsoriasis" as used herein refers to an eruption of reddish-brown papules with central scaling. It can last up to a few years, and clears without scarring.

In some examples of the method of the first and second aspect, upon administration of the at least one polycationic aliphatic amine, there is an increase in endogenous melanin content of melanocytes and/or an increase in the expression of melanogenesis-related genes and proteins.

Examples of melanogenesis-related genes include but are not limited to TYR, TYRP1, DCT and PMEL. Examples of melanogenesis-related proteins include but are not limited to proteins encoded by the above mentioned melanogenesis-related genes.

The TYR gene encodes for the protein named tyrosinase. Tyrosinase is an enzyme located in melanocytes. It is responsible for the first step of melanin production, by converting amino acid tyrosine to dopaquinone.

The TYRP1 gene encodes for the protein named tyrosinase-related protein 1. Tyrosinase-related protein 1 is an enzyme located in melanocytes. It is involved in the production of melanin, although its exact functions are unclear. It was suggested that this enzyme may help stabilize tyrosinase, and/or determine the shape of melanosomes.

The DCT gene is also known as the TYRP2 gene. It encodes for the protein named dopachrome tautomerase or tyrosinase-related protein 2. Dopachrome tautomerase converts dopachrome to its carboxylated derivative DHICA (5,6-dihydroxyindole-2-carboxylic acid). In the absence of dopachrome tautomerase, dopachrome will be spontaneously decarboxylated to produce DHI (5,6-dihydroxyindole), which in turn affects the properties of the melanins produced.

The PMEL gene encodes for the premalanosome protein (PMEL), also known as silver locus protein homolog (SILV). It is a melanocyte-specific type I transmembrane glycoprotein, and is often enriched in melanosomes. It plays an essential role in the structural organization of premelanosomes. For example, premalanosome protein is involved in generating internal matrix fibers that define the transition from Stage I to Stage II melanosomes. This protein undergoes a complex pattern of post-translational processing and modification that is essential to the proper function of the protein. A secreted form of the premalanosome protein that is released by proteolytic ectodomain shedding may be used as a melanoma-specifc serum marker. Alternate splicing results in multiple transcript variants.

There is also provided use of at least one polycationic aliphatic amine in the manufacture of a medicament for inducing or promoting darkening of the skin and/or melanogenesis, wherein the medicament is to be administered in a pharmaceutically effective amount. The at least one polycationic aliphatic amine and the pharmaceutically effect amount are as defined herein.

There is also provided use of at least one polycationic aliphatic amine in the manufacture of a medicament for treating a skin conditions or disorders, wherein the medicament is to be administered in a pharmaceutically effective amount. The at least one polycationic aliphatic amine, the skin disorder, and the pharmaceutically effective amount are as defined herein.

In a third aspect, there is provided a method of reducing or preventing darkening of the skin and/or melanogenesis, the method comprising administering at least one inhibitor of polycationic aliphatic amine in a pharmaceutically effective amount to a subject in need thereof. The polycationic aliphatic amine is as defined herein. There is also provided use of at least one inhibitor of polycationic aliphatic amine in the manufacture of a medicament for reducing or preventing darkening of the skin and/or melanogenesis, wherein the medicament is to be administered in a pharmaceutically effective amount.

In some examples, the at least one inhibitor of polycationic aliphatic amine could be an inhibitor of the transport of polycationic aliphatic amine, an inhibitor of the synthesis of polycationic aliphatic amine, an inhibitor of the catabolism of polycationic aliphatic amine, or combinations thereof.

Some non-limiting examples of the inhibitor of the transport of polycationic aliphatic amine are detailed in the figure below. These include, but are not limited to, trimer44NMe (a small molecule which acts as polyamine transport inhibitor (PTI)), trimer44, D-Lys-Spm, L-Lys-Spm, AMXT 1501 (an inhibitor of polyamine transport), Ant44, Ant44NMe, Ant444, triamide44, triamide444, triamide343, 44Bn44, MeN44Bn44NMe, mBn44, mBn444, N1-spermine-L-lysinylamide (ORI 1202), genistein, N-(2-mercaptoethyl) spermine-5-carboxamide (MESC), 2,2 1-dithiobis(N-ethyl-spermine-5-carboxamide) (DESC), N-[2,2'-Dithio(Ethyl,1'-Aminoethylspermine-S-carboxamide (DEASC), and combinations thereof. Exemplary structure of some of the polyamine transport inhibitors are shown below.

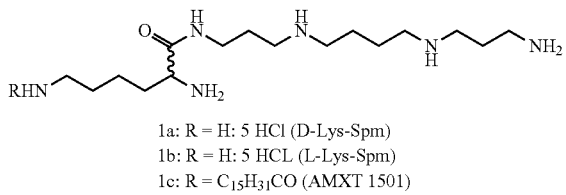

1a: R = H: 5 HCl (D-Lys-Spm)
1b: R = H: 5 HCL (L-Lys-Spm)
1c: R = C$_{15}$H$_{31}$CO (AMXT 1501)

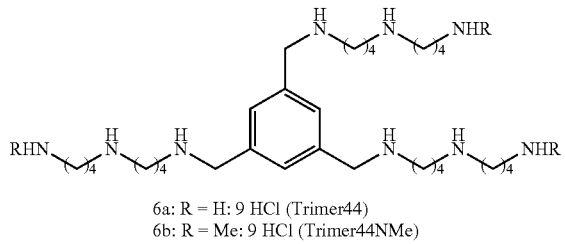

6a: R = H: 9 HCl (Trimer44)
6b: R = Me: 9 HCl (Trimer44NMe)

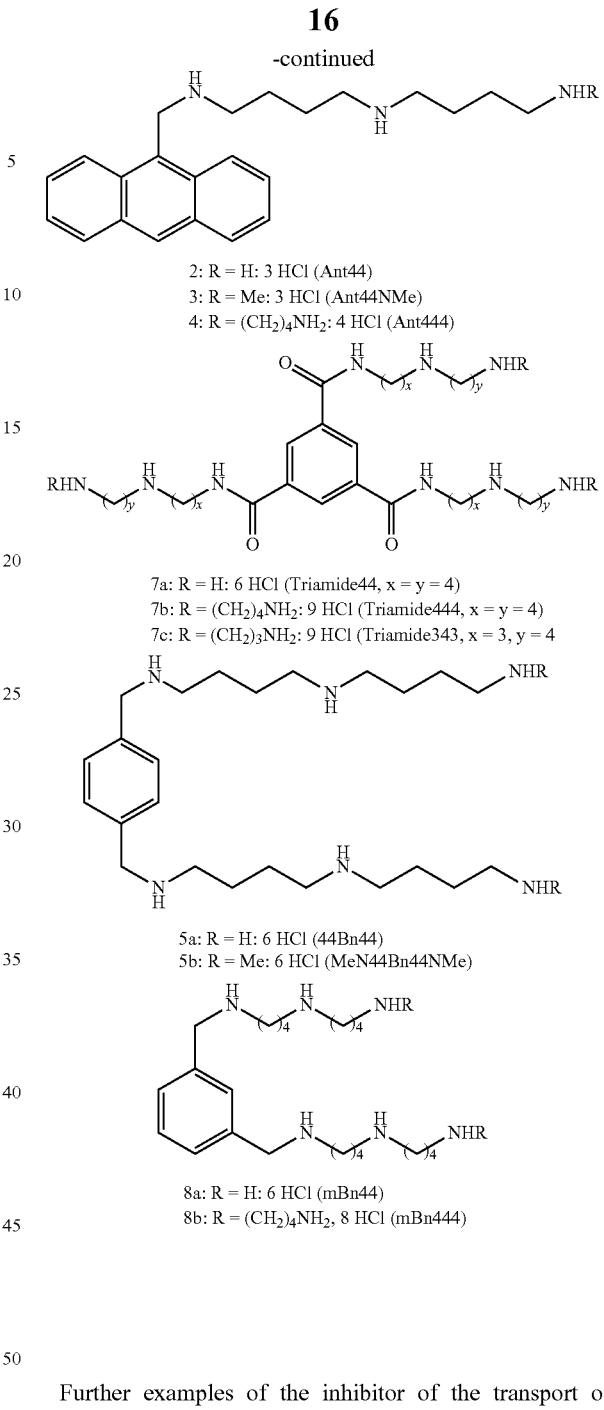

2: R = H: 3 HCl (Ant44)
3: R = Me: 3 HCl (Ant44NMe)
4: R = (CH$_2$)$_4$NH$_2$: 4 HCl (Ant444)

7a: R = H: 6 HCl (Triamide44, x = y = 4)
7b: R = (CH$_2$)$_4$NH$_2$: 9 HCl (Triamide444, x = y = 4)
7c: R = (CH$_2$)$_3$NH$_2$: 9 HCl (Triamide343, x = 3, y = 4)

5a: R = H: 6 HCl (44Bn44)
5b: R = Me: 6 HCl (MeN44Bn44NMe)

8a: R = H: 6 HCl (mBn44)
8b: R = (CH$_2$)$_4$NH$_2$, 8 HCl (mBn444)

Further examples of the inhibitor of the transport of polycationic aliphatic amine can be, but are not limited to, compounds according to formula A

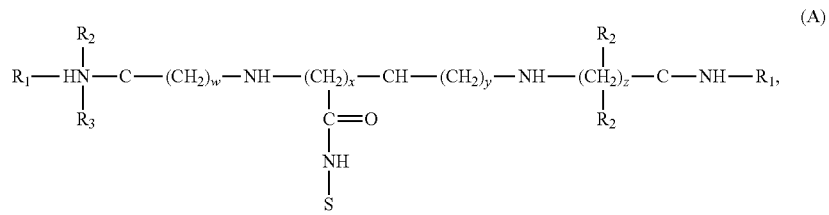

(A)

wherein $R_1$ and $R_1$, independently represent a hydrogen atom or an alkyl group having 1 to 2 carbon atoms, $R_2$, $R_2$, or $R_3$ and $R_3$ independently represent a hydrogen atom or a methyl group, w and z independently represent an integer of 2 or 3, x represents an integer from 0 to n, n represents an integer from 3 to 6, the sum of x and y equals n, and S represents a hydrogen atom or a molecule which cannot be captured by a natural polyamine transporter.

Another example of the inhibitor of the transport of polycationic aliphatic amine can be, but are not limited to, compounds according to formula (B)

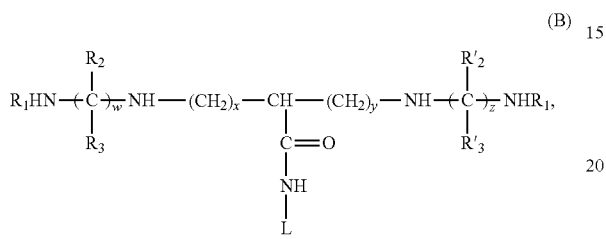
(B)

wherein $R_1$ and $R_1'$ independently represent a hydrogen atom or an alkyl group having 1 to 2 carbon atoms, $R_2$, $R_2'$, or $R_3$ and $R_3'$ independently represent a hydrogen atom or a methyl group, w and z independently represent an integer of 3 or 4, x represents an integer from 0 to n, y represents an integer from 0 to n, n represents an integer from 3 to 6, the sum of x and y equals n, and L represents a hydrogen atom or a molecule which cannot be captured by a natural polyamine transporter.

Even further examples of the inhibitor of the transport of polycationic aliphatic amine can be, but are not limited to, compounds according to formulas (I) and (II)

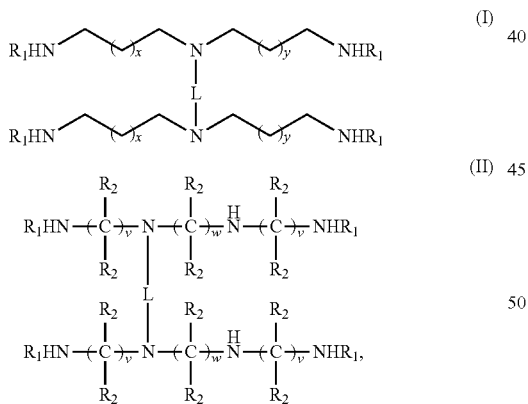
(I)
(II)

wherein L is a linker; $R_1$ is H, methyl, ethyl or propyl; $R_2$ is H or methyl; 0<x<3; 2<v<5; and 2<w<8. For example, compounds that fall under formula (I) can be, but are not limited to,

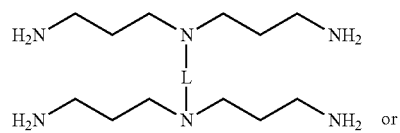

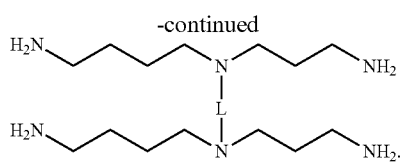

In one example, L is any one of the following

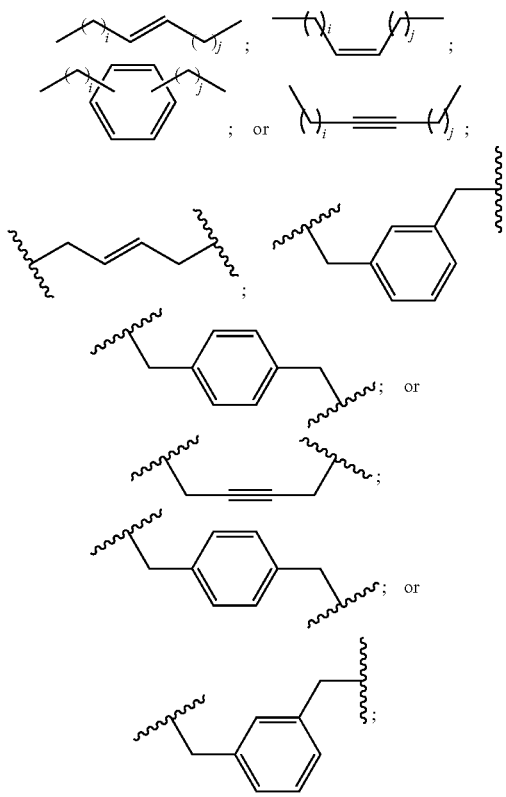

wherein 1<i+j<7.

In one specific example, the inhibitor of the transport of polycationic aliphatic amine is trimer44NMe. In another example, the inhibitor of polycationic aliphatic amine transport is AMXT 1501.

Some non-limiting examples of the inhibitor of the synthesis of polycationic aliphatic amine are: difluoromethylornithine (DFMO; an ODC1 inhibitor), ethylglyoxal bis (guanylhydrazone) (EGBG; an AMD1 inhibitor), methylglyoxal bis(guanylhydrazone) (MGBG; an AMD1 inhibitor), 4-amidoinoindan-1-one-2'-amidinhydrazone (SAM486A; an AMD1 inhibitor), and trans-4-methylcyclohexylamine (4MCHA; a spermine synthase inhibitor). In one specific example, the inhibitor of the synthesis of polycationic aliphatic amine is DFMO. DFMO is an irreversible inhibitor of ornithine decarboxylase (Odc). Odc is the rate-limiting enzyme in polycationic aliphatic amine synthesis, which catalyzes the decarboxylation of ornithine (a product of the urea cycle) to form putrescine. In another example, the function of ornithine decarboxylase 1 (ODC1) is inhibited. Thus, in a further example, the pharmaceutical composition disclosed herein comprises an ornithine decarboxylase 1 (ODC1) inhibitor. In yet another example, the inhibitor of ornithine decarboxylase 1 (ODC1) is, but is not limited to, siRNA, shRNA, (RS)-2,5-diamino-2-(difluoromethyl)pentanoic acid (α-difluoromethylornithine) (also known as DFMO; CAS no. 70052-12-9) and combinations thereof. In yet another example, the inhibitor of ornithine decarboxylase 1 (ODC1) is a shRNA. In another example, the inhibitor of ornithine decarboxylase 1 (ODC1) is a siRNA. In yet another example, the inhibitor of ornithine decarboxylase 1 (ODC1) is DFMO.

Some non-limiting examples of the inhibitor of the catabolism of polycationic aliphatic amine are N,N-bis(2,3-butadienyl)-1,4-butanediamine (MDL72527), N-ethyl-N'-[4-[4-[4-[[(E)-4-[4-[4-[4-(ethylamino)butylamino]butylamino]butylamino]butylamino]but-2-enyl]amino]butylamino]butylamino]butyl]butane-1,4-diamine (CGC-11144), N-(3-aminopropyl)-N'-2,3-butadienyl-1,4-butanediamine (N(8)-butadienyl Spd) and N-[3-(2,3-butadienylamino)propyl]-1,4-butanediamine (N(1)-butadienyl Spd).

In some examples of the aspect, the pharmaceutically effective amount of the at least one inhibitor of polycationic aliphatic amine to be administered is between 0.06 μmol to 3 mol, or between 0.03 μmol to 2.4 mol, or between 0.6 μmol to 1.8 mol, or between 1.2 μmol to 1.2 mol, or between 1.8 μmol to 600 mmol, or between 2.4 μmol to 540 mmol, or between 3 μmol to 480 mmol, or between 3.6 μmol to 420 mmol, or between 4.2 μmol to 360 mmol, or between 4.8 μmol to 300 mmol, or between 5.4 μmol to 240 mmol, or between 6 μmol to 180 mmol, or between 12 μmol to 120 mmol, or between 18 μmol to 60 mmol, or between 24 μmol to 54 mmol, or between 30 μmol to 48 mmol, or between 24 μmol to 42 mmol, or between 42 μmol to 36 mmol, or between 48 μmol to 30 mmol, or between 54 μmol to 24 mmol, or between 60 μmol to 18 mmol, or between 90 μmol to 6 mmol, or between 120 μmol to 6 mmol, or between 150 μmol to 5.4 mmol, or between 180 μmol to 4.8 mmol, or between 210 μmol to 4.2 mmol, or between 240 μmol to 3.6 mmol, or between 270 μmol to 3 mmol, or between 300 μmol to 2.4 mmol, or between 360 μmol to 1.8 mmol, or between 420 μmol to 1.2 mmol, or between 480 μmol to 600 μmol, or at about 0.06 μmol, or at about 0.3 μmol, or at about 0.6 μmol, or at about 3 μmol, or at about 6 μmol, or at about 9 μmol, or at about 12 μmol, or at about 15 μmol, or at about 18 μmol, or at about 21 μmol, or at about 24 μmol, or at about 27 μmol, or at about 30 μmol, or at about 60 μmol, or at about 90 μmol, or at about 120 μmol, or at about 150 μmol, or at about 180 μmol, or at about 210 μmol, or at about 240 μmol, or at about 270 μmol, or at about 300 μmol, or at about 360 μmol, or at about 420 μmol, or at about 480 μmol, or at about 540 μmol, or at about 600 μmol, or at about 900 μmol, or at about 1.5 mmol, or at about 2.1 mmol, or at about 2.7 mmol, or at about 3.3 mmol, or at about 3.9 mmol, or at about 4.5 mmol, or at about 5.1 mmol, or at about 5.7 mmol, or at about 6 mmol, or at about 30 mmol, or at about 60 mmol, or at about 90 mmol, or at about 120 mmol, or at about 150 mmol, or at about 180 mmol, or at about 210 mmol, or at about 240 mmol, or at about 270 mmol, or at about 300 mmol, or at about 360 mmol, or at about 420 mmol, or at about 480 mmol, or at about 540 mmol, or at about 600 mmol, or at about 900 mmol, or at about 1.2 mol, or at about 1.5 mol, or at about 1.8 mol, or at about 2.1 mol, or at about 2.4 mol, or at about 2.7 mol, or at about 3 mol. In some examples, the concentration of the at least one inhibitor of polycationic aliphatic amine is between 0.01 μM to 500 mM, or between 0.05 μM to 400 mM, or between 0.1 μM to 300 mM, or between 0.2 μM to 200 mM, or between 0.3 μM to 100 mM, or between 0.4 μM to 90 mM, or between 0.5 μM to 80 mM, or between 0.6 μM to 70 mM, or between 0.7 μM to 60 mM, or between 0.8 μM to 50 mM, or between 0.9 μM to 40 mM, or between 1 μM to 30 mM, or between 2 μM to 20 mM, or between 3 μM to 10 mM, or between 4 μM to 9 mM, or between 5 μM to 8 mM, or between 6 μM to 7 mM, or between 7 μM to 6 mM, or between 8 μM to 5 mM, or between 9 μM to 4 mM, or between 10 μM to 3 mM, or between 15 μM to 1 mM, or between 20 μM to 1 mM, or between 25 μM to 900 μM, or between 30 μM to 800 μM, or between 35 μM to 700 μM, or between 40 μM to 600 μM, or between 45 μM to 500 μM, or between 50 μM to 400 μM, or between 60 μM to 300 μM, or between 70 μM to 200 μM, or between 80 μM to 100 μM, or at about 0.01 μM, or at about 0.05 μM, or at about 0.1 μM, or at about 0.5 μM, or at about 1 μM, or at about 1.5 μM, or at about 2 μM, or at about 2.5 μM, or at about 3 μM, or at about 3.5 μM, or at about 4 μM, or at about 4.5 μM, or at about 5 μM, or at about 10 μM, or at about 15 μM, or at about 20 μM, or at about 25 μM, or at about 30 μM, or at about 35 μM, or at about 40 μM, or at about 45 μM, or at about 50 μM, or at about 60 μM, or at about 70 μM, or at about 80 μM, or at about 90 μM, or at about 100 μM, or at about 150 μM, or at about 250 μM, or at about 350 μM, or at about 450 μM, or at about 550 μM, or at about 650 μM, or at about 750 μM, or at about 850 μM, or at about 950 μM, or at about 1 mM, or at about 5 mM, or at about 10 mM, or at about 15 mM, or at about 20 mM, or at about 25 mM, or at about 30 mM, or at about 35 mM, or at about 40 mM, or at about 45 mM, or at about 50 mM, or at about 60 mM, or at about 70 mM, or at about 80 mM, or at about 90 mM, or at about 100 mM, or at about 150 mM, or at about 200 mM, or at about 250 mM, or at about 300 mM, or at about 350 mM, or at about 400 mM, or at about 450 mM, or at about 500 mM.

In some examples of the third aspect, the subject in need thereof is suffering from darkening of the skin and/or melanogenesis associated with pregnancy, inflammation, yeast infection, or aging.

There is also provided use of at least one inhibitor of polycationic aliphatic amine in the manufacture of a medicament for reducing darkening of the skin and/or melanogenesis associated with pregnancy, inflammation, yeast infection, or aging, wherein the medicament is to be administered in a pharmaceutically effective amount. The at least one inhibitor of polycationic aliphatic amine and the pharmaceutical effective amount of the at least one inhibitor of polycationic aliphatic amine are as defined herein.

It is common for a subject to develop melasma during pregnancy. The term "melasma", as used herein, is also known as chloasma or the mask of pregnancy, which appears as dark, irregular well demarcated hyper-pigmented macules to patches, commonly found on the upper cheek, nose, lips, upper lip, forehead, and other parts of the body that are exposed to the sun.

Darkening of the skin and/or melanogenesis associated with inflammation is commonly known as post-inflammatory hyperpigmentation (PIH). It is an acquired hypermelanosis occurring after cutaneous inflammation or injury. PIH results from the overproduction of melanin or an irregular dispersion of pigment after cutaneous inflammation. PIH typically manifests as macules or patches in the same distribution as the initial inflammatory process.

Darkening or lightening of the skin (also known as hyperpigmentation or hypopigmentation) can be associated with fungal infection, which is then considered to be a type of a skin condition known as tinea versicolor, also termed pityriasis versicolor. It can be caused by infection with fungi, for example, of the genus *Malassezia*, such as, but not limited to, *Malassezia globosa* and *Malassezia furfur*. Hyperpigmentation commonly appears as brown or reddish-brown patches, and is generally caused by chemicals secreted by the yeast. Other infections caused by yeast species, which also present with hyperpigmentation or hypopigmentation, can be treated according to the method claimed herein.

Darkening of the skin or hyperpigmentation associated with aging is commonly known as solar lentigo, which appears as patches of darkened skin. It results from exposure to UV radiation, which causes local proliferation of melanocytes and accumulation of melanin within the keratinocytes. Solar lentigos are common in people over the age of 40 years. Sometimes it is also known as an "old age spot" or "senile freckle".

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL EXAMPLES

The following examples illustrate methods by which aspects of the invention may be practiced or materials suitable for practice of certain embodiments of the invention may be prepared.

Example 1—Polycationic Aliphatic Amine Putrescine Increases the Melanin Content of the Melanocytes Methods
Cell Culture Human epidermal melanocytes from adult donor (Hema-LP) were purchased from Life Technologies. The cells were grown in 254 media with HMGS-2 and calcium chloride supplements in a humidified incubator containing 5% $CO_2$ according to the manufacturer's instruction. For putrescine treatments, the cells were plated at an approximate density of $20,000/cm^2$ the day before. Fresh media was added along with the respective drugs reconstituted in water (putrescine was purchased from Sigma Aldrich) to the cell cultures on day 0 and day 3 of experiment.

Melanin Quantification $2 \times 10^5$ cells were dissolved in 1 M sodium hydroxide solution and incubated at 80° C. for 2 hours. The absorbance of the cell lysates was measured at 405 nm in a microplate well reader.

Results

When normal human primary epidermal melanocytes from adult light pigmented donor (NHEM-aLP) cells were treated with 2 mM putrescine, every 3 days for 6 days, there was a drastic darkening effect that can be observed visually in the melanocytes (FIG. 1A). They became larger and flatter and displayed an increased number of dendrites (FIG. 1B). This phenotype is typically observed on treatment of NHEM with the melanogenic agents α-MSH, ACTH or endothelin-1, where the bipolar or tripolar melanocytes become more dendritic upon treatment. For melanin quantification, when the cell pellets were dissolved in NaOH solution, the cell lysate of the treated cells appeared darker when compared to the control and the melanin content in them was significantly increased up to 1.5-2 fold (FIG. 1C). These results suggest that there is an increase in the melanin content of the melanocytes when treated with the polycationic aliphatic amine putrescine.

Example 2—Polycationic Aliphatic Amine Putrescine Increases the Expression of Melanogenesis Related Genes and Proteins in Melanocytes Methods
Real Time PCR Total RNA was extracted from the cells using RNAeasy (Qiagen) according to manufacturer's instructions. 500 ng of total RNA was converted to complimentary DNA using RevertAid First Strand cDNA synthesis kit (Thermo Scientific). It was diluted 1:25, and 4 ul of the diluted mixture was used as a template with specific primers using Luminaris Colour HiGreen Hi ROX master mix (Thermo Fisher Scientific) for qRT-PCR on an ABI PRISM 7900 sequence detection system. The forward and reverse primers used were 5'-TGCACAGAGAGACGACTCTTG-3' (SEQ ID NO: 1) and 5'-GGCATGGACTGTGGTCATGAG-3' (SEQ ID NO: 2) for TYR, 5'-TCTCTGGGCTGTATCTTCTTCC-3' (SEQ ID NO: 3) and 5'-GTCTGGGCAACACATAC-CACT-3' (SEQ ID NO: 4) for TYRP1, 5'-CTTGGGCTGCAAAATCCTGC-3' (SEQ ID NO: 5) and 5'-CAGCACTCCTTGTTCACTAGG-3' (SEQ ID NO: 6) for DCT, 5'-AGTGCCTACTACAGAAGTTGTGG-3' (SEQ ID NO: 7) and 5'-CACAGGTGCAGTGCTTATGAC-3' (SEQ ID NO: 8) for PMEL respectively. Expression levels detected by qPCR were normalized with ribosomal protein LP0 or L13A.

Western Blotting

The cells were lysed in RIPA buffer, and concentration of the cell lysate was determined by Pierce BCA Protein Assay Kit (Thermo Scientific). 10 or 30 ug was separated in a 10% Criterion™ TGX Stain-Free™ gels (Biorad) and transferred onto PVDF membrane (Biorad) using the semi-dry transfer technique. The membrane was blocked with 5% skim milk in TBST (0.1% Tween-20 (Sigma-Aldrich) in 1×TBS (0.1 M NaCl, 0.1 M Tris pH 7.4 in ddH2O; purchased from Biopolis Shared Facility) and incubated overnight at 4° C. with respective primary antibodies against TYR (sc-7833), TYRP1 (sc-10443), DCT (sc-10451) from Santa Cruz Biotechnology Inc and RPLP0 (AB126480) from Abcam at a dilution of 1:1000 in blocking buffer. The samples were then incubated with horseradish peroxidase-labeled anti-rabbit, or anti-goat IgG (Santa Cruz Biotechnology, Inc) at a dilution 1:5000 for 1 hour at 4° C. and immunoreactive bands were detected with enhanced chemiluminescent substrate (Thermo Fisher Scientific).

Results

Figure 2:
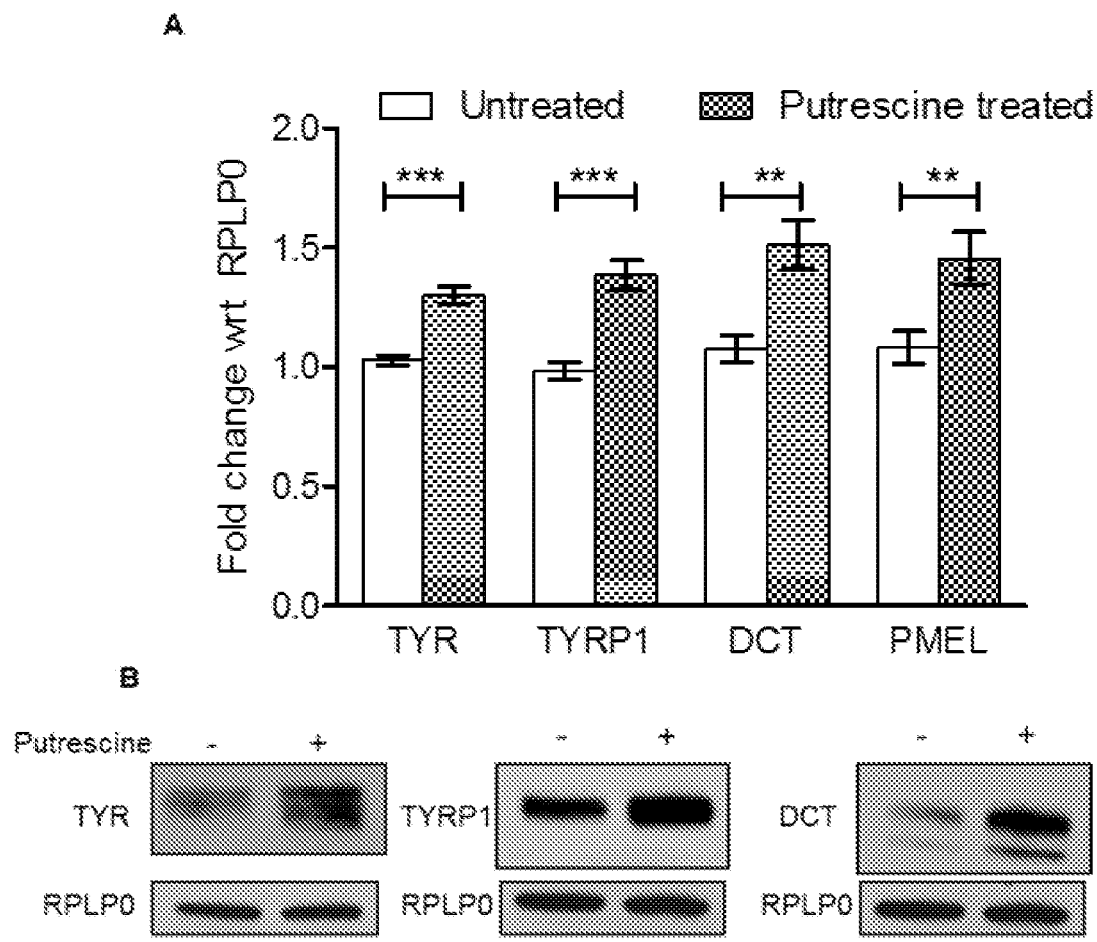
FIG. 2 shows the effect of putrescine treatment on the expression of melanogenesis genes and proteins.

The treatment of NHEM-aLP cells with putrescine causes a significant increase in the mRNA expression levels of TYR, TYRP1, DCT and PMEL, which are important genes involved in melanogenesis (FIG. 2A). The respective protein levels of TYR, TYRP1 and DCT also increased drastically upon putrescine treatment when compared to the control (FIG. 2B), when analysed by western blotting. These results suggest that the polycationic aliphatic amine putrescine stimulated the expression of melanogenesis related genes and their respective protein levels in the melanocytes.

Example 3—Putrescine Increases the Pigmentation in a Reconstructed Human 3D Human Skin Model Methods The reconstructed epidermis (Denova Sciences) has normal human keratinocytes three dimensionally cultured at an air-liquid interface in a chemically defined medium, in the presence of melanocytes and fibroblasts. They were treated with 2 mM Putrescine for 14 days.

Results

Figure 3:
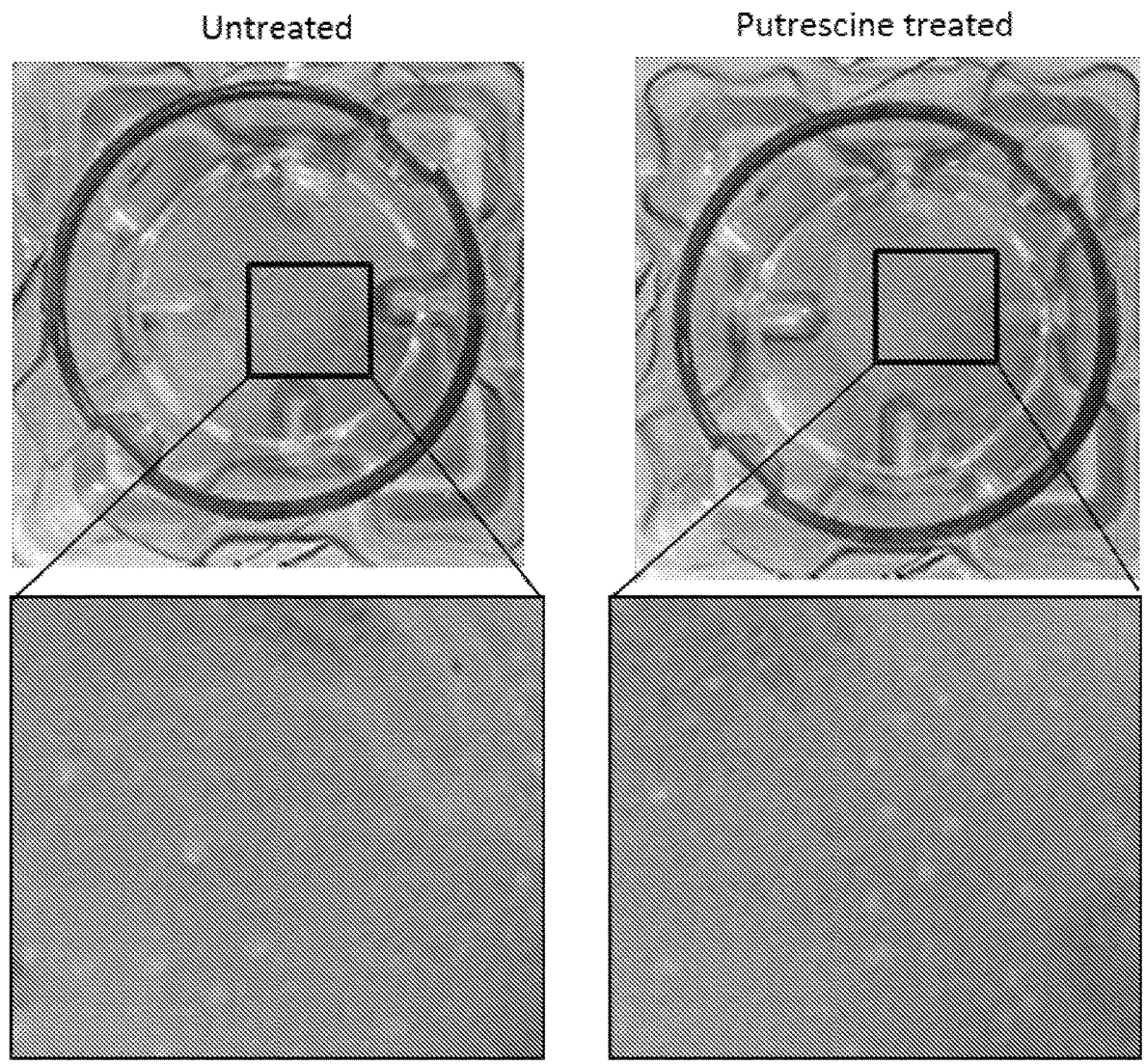
FIG. 3 shows representative images of the skin cultures without (right) and with (left) putrescine treatment. A visible increase in pigmentation in the putrescine treated skin culture can be seen. The bottom panel is an enlarged region of the box in the top panel. The results demonstrate that putrescine increases pigmentation in a reconstituted 3D human skin model.
Figure 4:
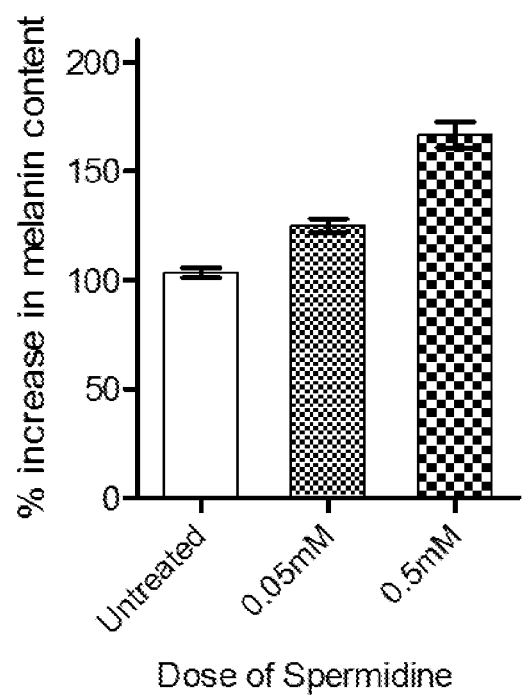
FIG. 4 is a bar chart showing the increase in melanin content when different doses of spermidine are used. The results demonstrate that spermidine causes a dose-dependent increase in the melanin content of the NHEM-aLP cells (n=4).
Figure 5:
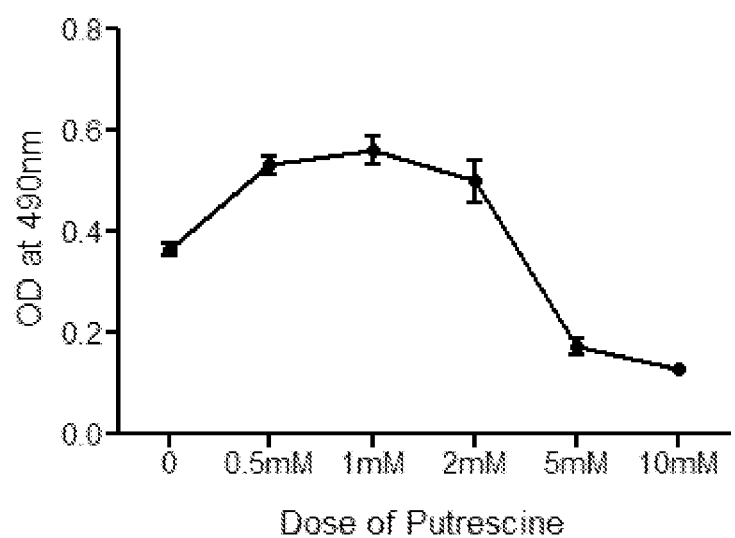
FIG. 5 shows the results of proliferation and cytotoxicity colorimetric assay performed on the NHEM-aLP cells with different doses of putrescine. n=3; error bar is mean±SEM. This data shows that the melanocytes can tolerate up to 2 mM concentration of putrescine, which in some situations may be considered to be a high dose. The assay performed was a (3-(4,5-dimethylthiazol-2-yl)-5-(3-carboxymethoxyphenyl)-2-(4-sulfophenyl)-2H-tetrazolium) assay, also known as an MTS assay, the information of which has provided in the experimental section of this application.

In a preliminary experiment, the reconstructed epidermis when treated with 2 mM Putrescine for 14 days showed an increase in pigmentation levels as compared to the control (FIG. 3).

Example 4—Polycationic Aliphatic Amine Spermidine Increases Melanin Content in Melanocytes Methods Cell Culture Human epidermal melanocytes from adult donor (Hema-LP) were purchased from Life Technologies. The cells were grown in 254 media with HMGS-2 and calcium chloride supplements in a humidified incubator containing 5% $CO_2$ according to the manufacturer's instruction. For spermidine treatments, the cells were plated at an approximate density of $20,000/cm^2$ the day before. Fresh media was added along with the respective drugs reconstituted in water (spermidine was purchased from Sigma Aldrich) to the cell cultures on day 0 and day 3 of experiment.

Melanin Quantification $2\times10^5$ cells were dissolved in 1M sodium hydroxide solution and incubated at 80° C. for 2 hours. The absorbance of the cell lysates was measured at 405 nm in a microplate well reader.

Results

When NHEM-aLP cells were treated with 0.05 mM and 0.5 mM of spermidine, every 3 days for 6 days, there was a dose dependant increase in melanin content of the cells. The maximum fold change was about 1.5-2 fold increase in 0.5 mM spermidine, similar to the observation for putrescine but at a 4 times lower concentration (0.5 mM) than putrescine (2 mM). This result suggests that there is also an increase in the melanin content of the melanocytes when treated with the polycationic aliphatic amine spermidine.

Example 5—Dosage of Polycationic Aliphatic Amine Putrescine

Methods

MTS Assay

A proliferation and cytotoxicity colorimetric assay was performed on the NHEM-aLP cells using the commercial MTS CellTiter 96® $AQ_{ueous}$ One Solution Cell Proliferation Assay (Promega). The cells were treated with varying doses of putrescine for 3 days. After 3 days the cells were incubated for 2 hours with MTS tetrazolium, which is reduced by viable cells to generate a colored formazan product. This product is soluble in cell culture media and is quantified by measuring the absorbance at 490 nm.

Results

The maximum dose of the polycationic aliphatic amine putrescine up to which the NHEM-aLP can survive was found to be 2 mM, using a cell cytotoxicity and proliferation assay. A mild proliferative effect is seen with doses between 0.5 mM and 2 mM of putrescine.

Figure 6:
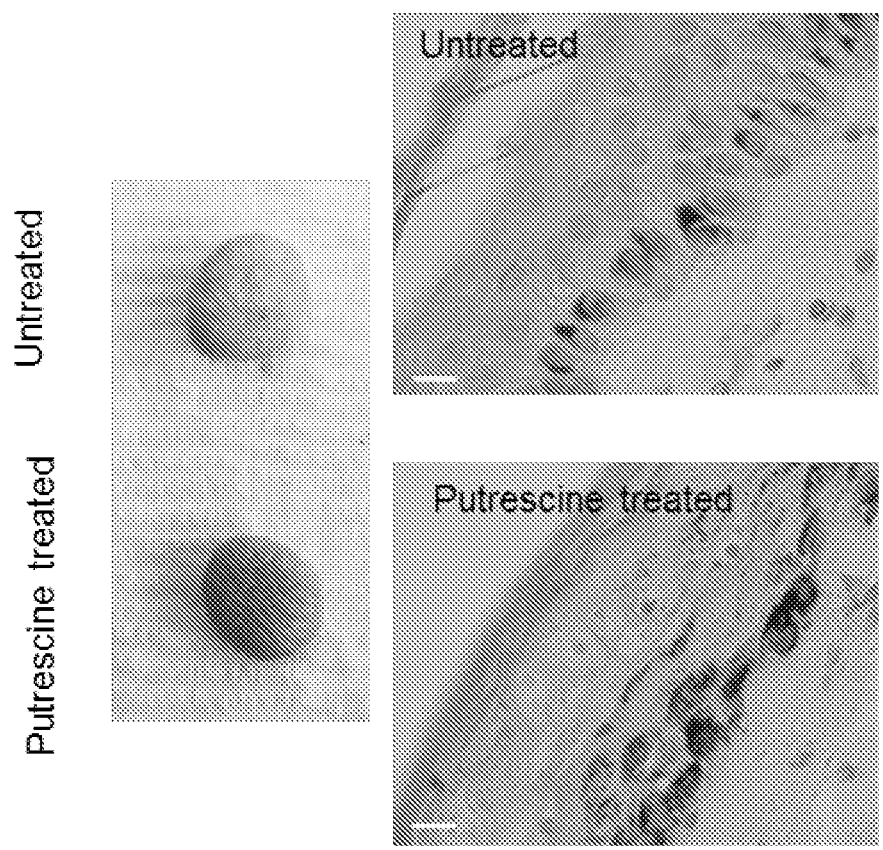
FIG. 6 shows the results of human abdominal skin biopsies incubated with and without putrescine. Samples of human abdominal skin biopsies were incubated with and without putrescine for ten days. The skin was then imaged, followed by sectioning and staining with Fontana Mason stain, which stains for melanin. The results show that putrescine promoted darkening of the skin and resulted in an increase in melanin staining, both within the melanocytes and the neighboring keratinocytes. This demonstrates that putrescine drives melanogenesis in the melanocytes and the resulting melanin pigments are deposited onto the neighboring keratinocytes.

Example 6—Use of Polycationic Aliphatic Amines to Induce Darkening of the Skin by Promoting Melanogenesis In order to show that putrescine will promote pigmentation in human skin biopsies, human abdominal skin biopsies were incubated with and without putrescine for ten days. The skin was them imaged, followed by sectioning and staining with Fontana Mason stain which stains for melanin. The results shown that putrescine promoted darkening of the skin and an increase in melanin stain both within the melanocytes and within the neighboring keratinocytes. This data suggests that putrescine drives melanogenesis in the melanocytes, and the resulting melanin pigments are deposited onto the neighboring keratinocytes (FIG. 6).

Figure 7:
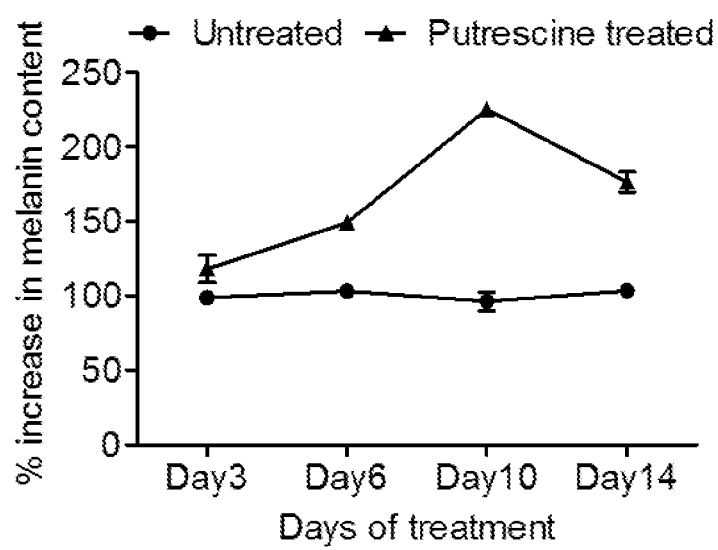
FIG. 7 is a graph showing the increase in melanin content after long-term treatment with putrescine. The results show that long-term culture of primary melanocytes with putrescine results in a sustained increase in melanin content, suggesting that putrescine promotes sustained melanogenesis.
Figure 8:
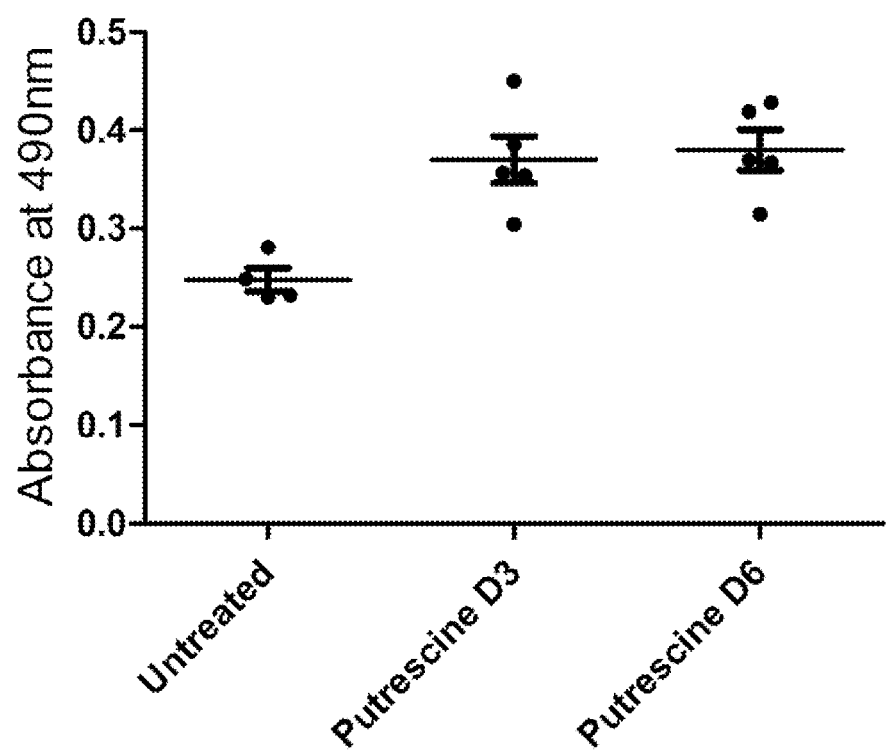
FIG. 8 is a dot plot showing the viability of cells untreated, treated for 3 days, or treated for 6 days with putrescine. The results show that there is no decrease in cell viability 3 days and 6 days after incubating with putrescine.

Long term culture of primary human melanocytes with putrescine results in a sustained increase in melanin content, with no decrease in viability 3 and 6 days after incubation (FIGS. 7 and 8). This data suggests that putrescine promotes sustained melanogenesis without compromising viability.

The above results show that putrescine drives pigmentation in melanocytes, suggesting that inhibition of polycationic aliphatic amines or their metabolites in melanocytes will inhibit pigmentation. This has clinical relevance in a number of different human conditions, including conditions where polycationic aliphatic amine levels or polycationic aliphatic amine metabolites are up or down regulated. These include melasma, post inflammatory hyperpigmentation, pregnancy associated pigmentation, yeast or bacterial associated pigmentation.

Figure 9:
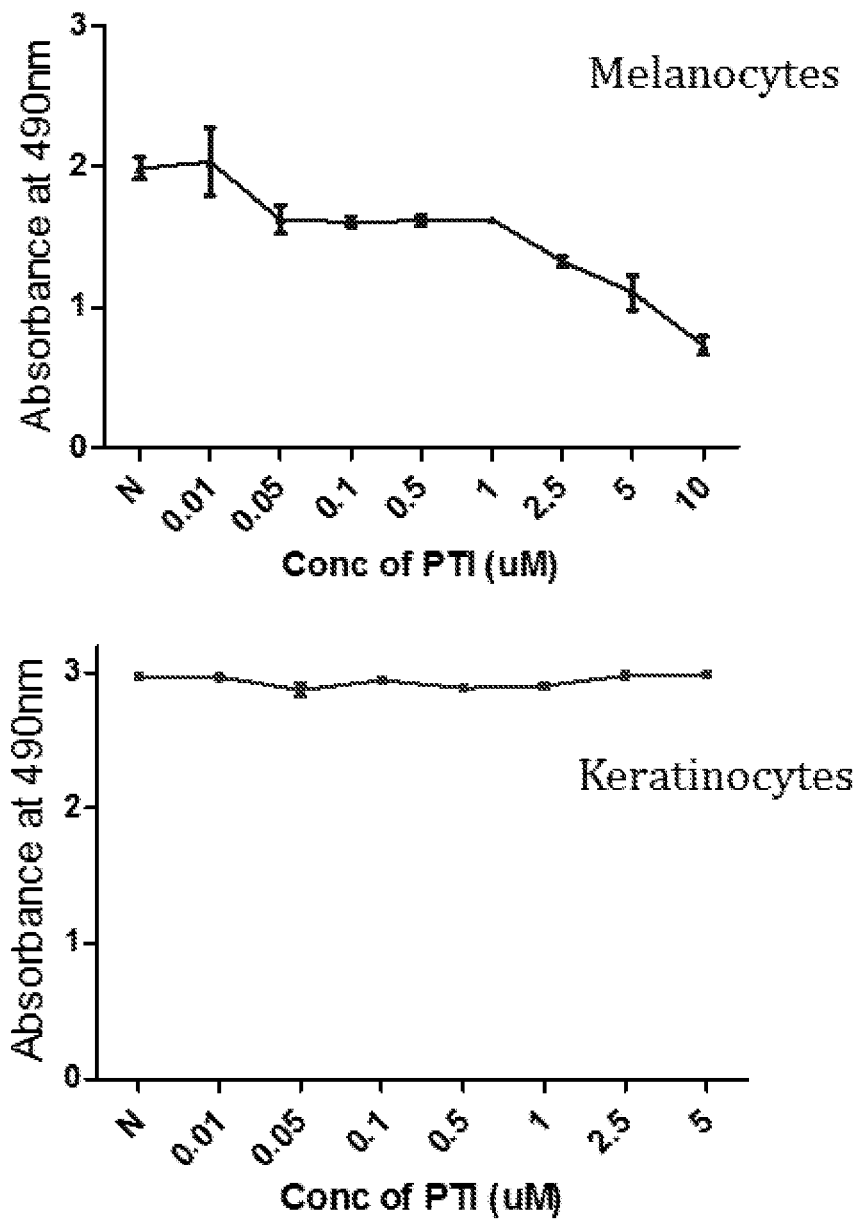
FIG. 9 shows the results of cell viability assay after the cells are being treated with a polycationic aliphatic amine transport inhibitor. Human keratinocytes and melanocytes were cultured in the presence of increasing concentrations of a polycationic aliphatic amine transport inhibitor, trimer44NMe. The cell viability was determined by an MTT assay. The results show that only melanocytes, but not keratinocytes, are sensitive to the polycationic aliphatic amine transport inhibitor (up to 5 µM). This suggests that melanocytes are largely dependent on the transport of polycationic aliphatic amines for survival, and are more sensitive to changes in the extracellular levels of polycationic aliphatic amines as compared to keratinocytes.
Figure 10:
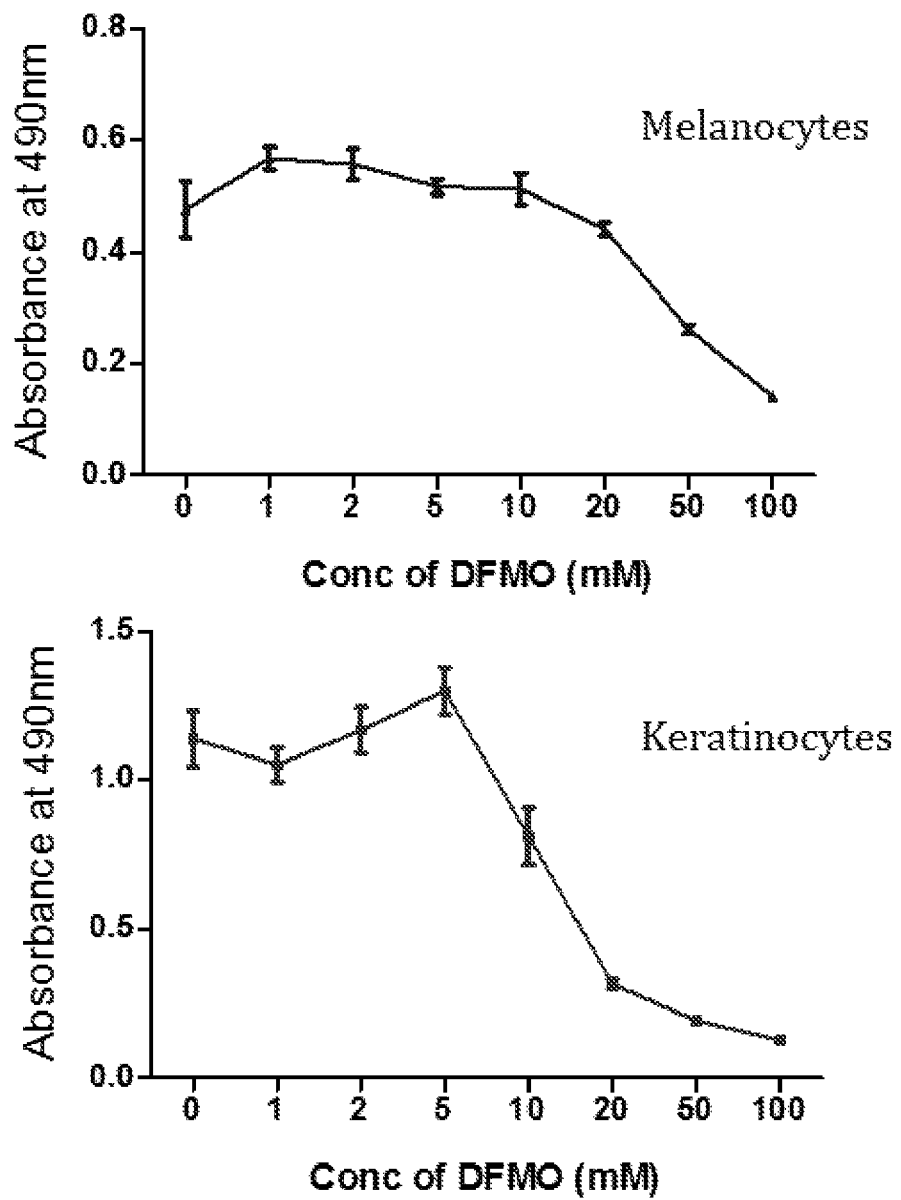
FIG. 10 shows the results of cell viability assay after the cells are being treated with DFMO (CAS no. 70052-12-9), an inhibitor of ornithine decarboxylase 1 (ODC1), a key enzyme in polycationic aliphatic amine synthesis. The cell viability was determined by an MTT assay. The results show that keratinocytes are sensitive to DFMO, and that melanocytes are comparatively insensitive to DFMO. This suggests that keratinocytes are largely dependent on the synthesis of polycationic aliphatic amines for survival.

Example 7—Use of Polycationic Aliphatic Amine Transport Inhibitors to Reduce/Prevent Pigmentation Human melanocytes are highly Dependent on polycationic aliphatic amine Import for Maintenance of Intracellular polycationic aliphatic amine Levels The import of polycationic aliphatic amines can be inhibited with the use of polycationic aliphatic amine transport inhibitors (PTI). Different cell types show varying degrees of sensitivity to polycationic aliphatic amine transport inhibitors. Different cell types also show differing sensitivity to the ODC1 inhibitor DFMO that inhibits intracellular synthesis of polycationic aliphatic amines. Human keratinocytes and melanocytes were cultured in the presence of increasing concentrations of a polycationic aliphatic amine transport inhibitor, trimer44NMe, or DFMO, and the cell viability was determined by an MTT assay. It was observed that while keratinocytes were sensitive to DFMO but not PTIs (up to 5 µM), melanocytes are comparatively insensitive to DFMO but highly sensitive to the polycationic aliphatic amine transport inhibitor (FIGS. 9 and 10). This suggests that keratinocytes depend mainly on the synthesis of polycationic aliphatic amines for survival, while melanocytes are largely dependent on transport of polycationic aliphatic amines for survival. The result also suggests that melanocytes are more sensitive to changes in the extracellular levels of polycationic aliphatic amines.

Putrescine is taken up by Cultured melanocytes

Figure 11:
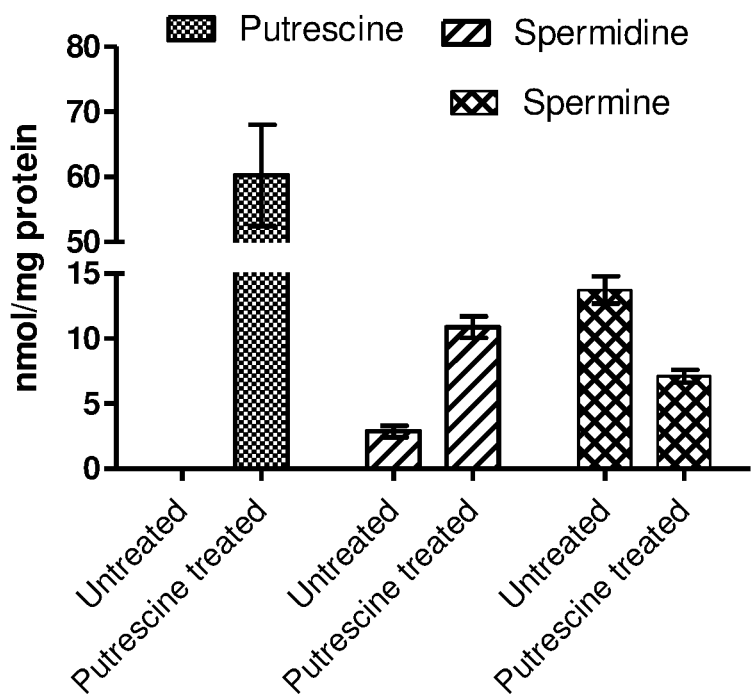
FIG. 11 is a bar chart showing the contents of different polycationic aliphatic amines in melanocytes cultured with and without putrescine. The results show that melanocytes import a significant quantity of putrescine, as intracellular levels are dramatically higher in treated cells than in non-treated cells. In addition to increased putrescine, there is also a decrease in the levels of spermine, indicating that polycationic aliphatic amine catabolism has been activated, which in turn would result in the generation of Acrolein and $H_2O_2$. Without being bound by theory, increased $H_2O_2$ and Acrolein may, at least in part, be the mechanism by which putrescine acts to promote pigmentation. Inhibition of polycationic aliphatic amine catabolism will reduce the generation of $H_2O_2$ and Acrolein from polycationic aliphatic amine catabolism, and could therefore be used to inhibit pigmentation.
Figure 12:
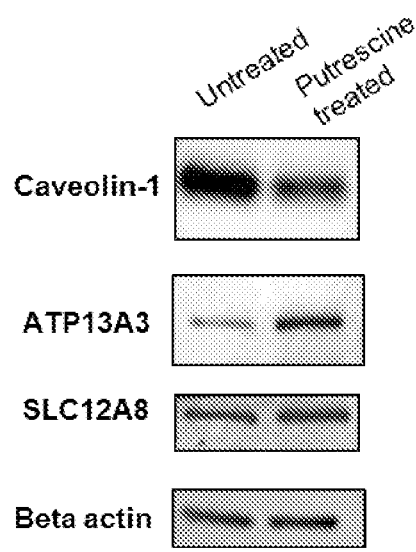
FIG. 12 shows that protein levels of polyamine transporters ATP13A3 and SLC11A8 increase in melanocytes on addition of putrescine while Caveolin-1 decreases. An increase in ATP13A3 and SLC12A8 and a decrease in Caveolin-1 are consistent with an increase in polyamine transport. These data further suggest that polyamine transport is essential for the polyamine mediated promotion of pigmentation.

To confirm that cultured human melanocytes do take up putrescine, the polycationic aliphatic amine content was measured in melanocytes cultured with and without putrescine. It was observed that melanocytes import a significant quantity of putrescine, as intracellular levels of putrescine in melanocytes cultured with putrescine are dramatically higher than in non-treated cells (FIG. 11).

Figure 13:
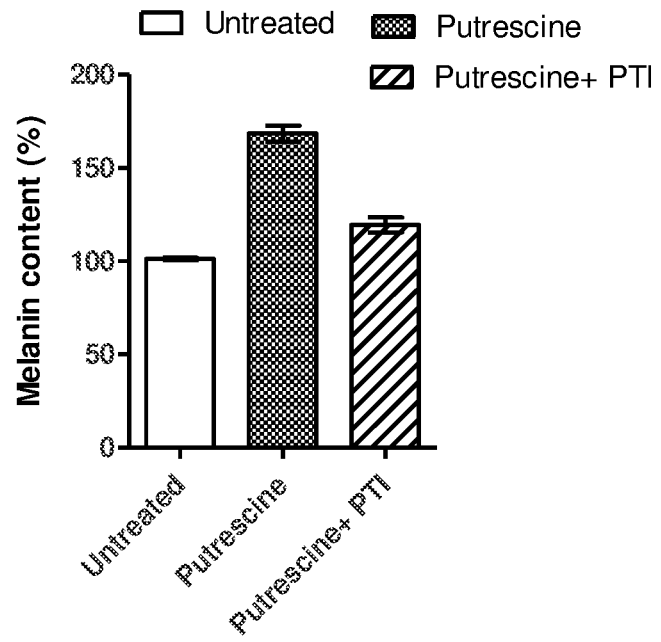
FIG. 13 is a bar chart showing the melanin content of untreated melanocytes, melanocytes treated with putrescine alone, and melanocytes treated with a combination of putrescine and the polycationic aliphatic amine transport inhibitor, trimer44NMe. The inclusion of the polycationic aliphatic amine transport inhibitor blocked the ability of putrescine to promote pigmentation, demonstrating that polycationic aliphatic amine transport is required for the putrescine induction of melanogenesis in melanocytes. The data further suggests that a polycationic aliphatic amine transport inhibitor may be able to decrease pigmentation in human skin.

Inhibition of polycationic aliphatic amine Transport Prevents putrescine induced Pigmentation To confirm that import of putrescine is required for the pigmentation phenotype observed in melanocytes, human primary melanocytes were cultured with putrescine with and without a polycationic aliphatic amine transport inhibitor (trimer44NMe). The inclusion of the polycationic aliphatic amine transport inhibitor blocked the ability of putrescine to promote pigmentation, demonstrating that polycationic aliphatic amine transport is required for the putrescine induction of melanogenesis in melanocytes (FIG. 13). This data further suggests that a polycationic aliphatic amine transport inhibitor may be able to decrease pigmentation in human skin.

Figure 14:
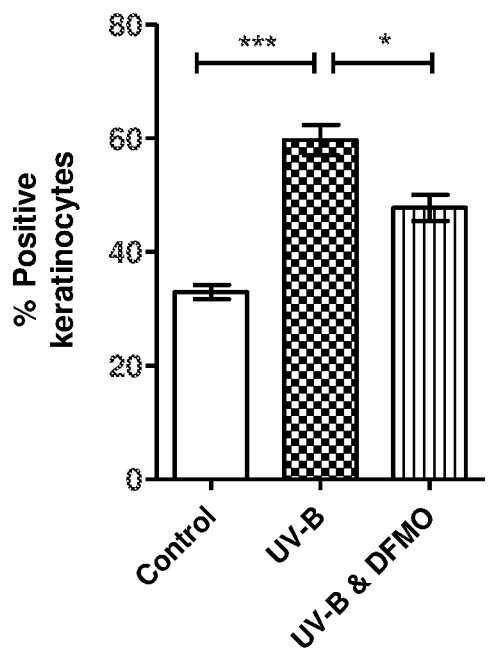
FIG. 14 is a bar chart showing the percentage of melanin-containing keratinocytes in different treatment groups. Human melanocytes and keratinocytes are grown in co-culture. Upon UV induction, keratinocytes signal to melanocytes to increase melanogenesis. The results show that inhibition of polycationic aliphatic amine synthesis by ODC1 inhibitor DFMO inhibits UV induced pigmentation in keratinocytes.

Example 8—Use of Polycationic Aliphatic Amine Biosynthesis Inhibitors to Reduce/Prevent Pigmentation On UV induction, keratinocytes signal to melanocytes to increase melanogenesis. This can be modeled through co-culture of human melanocytes and keratinocytes under UV induction. The results show that inhibition of polycationic aliphatic amine synthesis with DFMO in co-cultured keratinocytes and melanocytes inhibits UV induced pigmentation, suggesting that polycationic aliphatic amines play a role in this process (FIG. 14). This data suggests that inhibition of polycationic aliphatic amine biosynthesis, for example with DFMO, will inhibit pigmentation.

Figure 15:
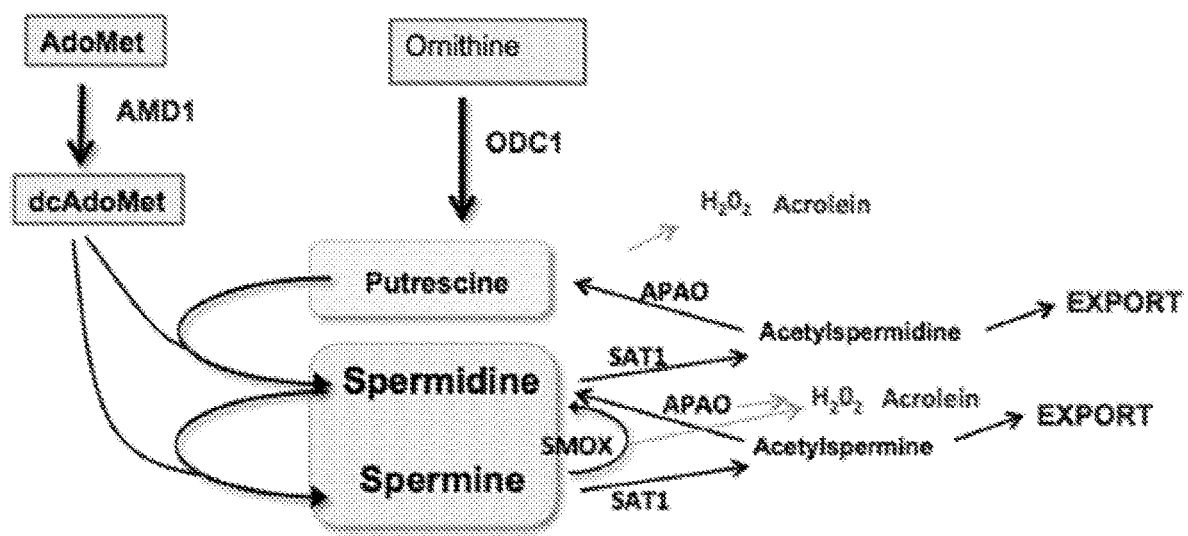
FIG. 15 is a diagram depicting the overview of the polycationic aliphatic amines biosynthesis and catabolic pathway. Mammalian cells can either synthesize polycationic aliphatic amines downstream of the urea cycle, or they can be imported into the cell through specific transporters. When the intracellular levels of polycationic aliphatic amines are too high, they are catabolized by the enzymes SMOX and SAT1. Spermine is catabolized directly to spermidine by the SMOX enzyme with $H_2O_2$ and Acrolein being the major byproducts. Spermine can also be acetylated by SAT1, and the resulting acetylated spermine is, in turn, either exported from the cell, or further catabolized by PAOX (Peroxisomal N(1)-acetyl-spermine/spermidine oxidase, also known as APOA) with the generation of $H_2O_2$ and Acrolein. SAT1 and APAO/PAOX can also catabolize spermidine to putrescine in a similar manner. A balance of synthesis, catabolism, import and export maintains and controls intracellular polycationic aliphatic amine levels.

Example 9—Use of Inhibitors of Polycationic Aliphatic Amine Catabolism to Reduce/Prevent Pigmentation Mammalian cells can synthesize polycationic aliphatic amines downstream of the UREA cycle or they can be imported into the cell through specific transporters. When the levels of polycationic aliphatic amines are too high, the polycationic aliphatic amines are catabolized by the enzymes SMOX and SAT1. Spermine is catabolized directly to spermidine by the SMOX enzyme with $H_2O_2$ and Acrolein being the major by products. Spermine can also be acetylated by SAT1, and then acetylated spermine in turn is either exported from the cell or further catabolized by PAOX with the generation of $H_2O_2$ and Acrolein. SAT1 and APAO can also catabolize spermidine to putrescine in a similar manner. A balance of synthesis, catabolism, import and export maintains and controls intracellular polycationic aliphatic amine levels (FIG. 15).

It is observed that melanocytes can uptake high levels of putrescine (FIG. 11). In addition to increased putrescine, there is also a decrease in the levels of spermine, strongly indicting that polycationic aliphatic amine catabolism has been activated, which would result in the generation of Acrolein and $H_2O_2$. It is likely that increased $H_2O_2$ and Acrolein may, at least in part, be the mechanism by which putrescine acts to promote pigmentation. Inhibition of polycationic aliphatic amine catabolism will reduce the generation of $H_2O_2$ and Acrolein from polycationic aliphatic amine catabolism and could be used to inhibit pigmentation.

Example 10—Aberrant Regulation of the Polycationic Aliphatic Amine Pathway by be Involved in the Development of Vitiligo Accumulation of putrescine can be achieved through two pathways—one through decarboxylation of ornithine by the enzyme ODC1, and one through catabolism of spermidine and spermine by the enzyme SSAT/SMOX. It is known that the catabolism of polycationic aliphatic amines can produce peroxides. Thus, accumulation of putrescine through the catabolism pathway may increase oxidative stress to the cells.

There is some evidence in literature that the death of vitiligo melanocytes may be due to excessive oxidative stress. It is also known that vitiligo melanocytes may be more vulnerable to oxidants. Vitiligo patients have higher levels of $H_2O_2$, an imbalance in their intracellular redox status, and levels of antioxidants are also altered in vitiligo patients.

Hence it is possible that the levels of polycationic aliphatic amines and their regulators are not normal in the vitiligo patients, and there may be a role of polycationic aliphatic amines in vitiligo. The levels of SAT1/APAO/SMOX may be higher in the perilesional skin, as there is evidence that the perilesional keratinocytes have higher ROS production compared to lesional or normal skin of vitiligo patients.

What is claimed is:

1. A method of reducing darkening of the skin and/or melanogenesis, the method comprising administering at least one inhibitor of polycationic aliphatic amine in a pharmaceutically effective amount to a subject in need thereof.

2. The method of claim 1, wherein the subject is suffering from darkening of the skin and/or melanogenesis associated with pregnancy, inflammation, yeast infection, or aging.

3. The method of claim 1, wherein the at least one inhibitor of polycationic aliphatic amine is selected from the group consisting of: an inhibitor of the transport of polycationic aliphatic amine, an inhibitor of the synthesis of polycationic aliphatic amine, an inhibitor of the catabolism of polycationic aliphatic amine, and combinations thereof.

4. The method of claim 3, wherein the inhibitor of the transport of polycationic aliphatic amine is trimer44NMe.

5. The method of claim 3, wherein the inhibitor of the synthesis of polycationic aliphatic amine is difluoromethylornithine (DFMO).

6. The method of claim 1, wherein the at least one inhibitor of polycationic aliphatic amine is administered in a pharmaceutical composition.

7. The method of claim 6, wherein the pharmaceutical composition is provided as pastes, powders, dressings, creams, plasters, solutions, patches, gels, suspensions, aqueous liquid suspensions, non-aqueous liquid suspensions, oil-in-water emulsions, water-in-oil liquid emulsions, solutions, sterile solids, crystalline solids, amorphous solids, solids for reconstitution or combinations thereof.

8. The method of claim 6, wherein the pharmaceutical composition is a dermatological composition.

9. The method of claim 1, wherein the method is used for cosmetic purposes.

10. The method of claim 6, wherein the pharmaceutical composition is administered intradermally, cutaneously, subcutaneously, topically, transdermally, or any combination thereof.

11. The method of claim 2, wherein the subject is suffering from melasma.

12. The method of claim 2, wherein the subject is suffering from post inflammatory hyperpigmentation.

13. The method of claim 2, wherein the subject is suffering from solar lentigo.

14. The method of claim 3, wherein the inhibitor of the synthesis of polycationic aliphatic amine is an ornithine decarboxylase 1 (ODC1) inhibitor.

15. A method of reducing darkening of the skin and/or melanogenesis, the method comprising administering at least one ornithine decarboxylase 1 (ODC1) inhibitor in a pharmaceutically effective amount to a subject in need thereof, wherein the subject is suffering from melasma, post inflammatory hyperpigmentation, or solar lentigo.

16. The method of claim 15, wherein the subject is suffering from melasma.

17. A method of reducing darkening of the skin and/or melanogenesis, the method comprising administering difluoromethylornithine (DFMO) in a pharmaceutically effective amount to a subject in need thereof, wherein the subject is suffering from melasma, post inflammatory hyperpigmentation, or solar lentigo.

18. The method of claim 17, wherein the subject is suffering from melasma.

* * * * *